US008100842B2

(12) United States Patent
Rousso

(10) Patent No.: US 8,100,842 B2
(45) Date of Patent: Jan. 24, 2012

(54) PORTABLE DEVICE FOR THE ENHANCEMENT OF CIRCULATION

(76) Inventor: Benny Rousso, Rishon LeZion (IL)

( * ) Notice: Subject to any disclaimer, the term of this patent is extended or adjusted under 35 U.S.C. 154(b) by 1335 days.

(21) Appl. No.: 11/575,998

(22) PCT Filed: Sep. 26, 2005

(86) PCT No.: PCT/IL2005/001028

§ 371 (c)(1), (2), (4) Date: Mar. 29, 2007

(87) PCT Pub. No.: WO2006/033114

PCT Pub. Date: Mar. 30, 2006

(65) Prior Publication Data

US 2008/0015630 A1 Jan. 17, 2008

(30) Foreign Application Priority Data

Sep. 26, 2004 (IL) ........................................ 164285

(51) Int. Cl.
*A61B 17/12* (2006.01)

(52) U.S. Cl. ........................ 601/151; 601/148; 606/202

(58) Field of Classification Search .................. 601/6, 8, 601/9, 11, 133, 148, 149, 150, 151, 152; 602/13; 606/201, 202
See application file for complete search history.

(56) References Cited

U.S. PATENT DOCUMENTS

| | | | |
|---|---|---|---|
| 3,853,121 | A | 12/1974 | Mizrachy et al. |
| 6,135,116 | A | 10/2000 | Vogel et al. |
| 6,290,662 | B1 | 9/2001 | Morris et al. |
| 6,494,852 | B1 | 12/2002 | Barak et al. |
| 2004/0073146 | A1 | 4/2004 | Weintraub et al. |

*Primary Examiner* — Quang D Thanh

(57) ABSTRACT

A portable device for enhancing circulation in a limb by applying intermittent squeezing force on the limb, the device comprising at least one inflatable fluid-cell having a proximal face and a distal face; a rigid member juxtaposed with the distal face of the air-cell, the rigid member is having two lateral sides; at least one adjustable strap connectable to the lateral ends of the rigid member for encircling the limb; and a mechanism for intermittently inflating and deflating the at least one fluid cell.

65 Claims, 17 Drawing Sheets

PORTABLE DEVICE FOR THE ENHANCEMENT OF CIRCULATION

RELATED APPLICATIONS

The present application is related to Israel Patent Application serial number 160185 filed on 2 Feb., 2004 titled "A PORTABLE DEVICE FOR THE ENHANCEMENT OF CIRCULATION OF BLOOD AND LYMPH FLOW IN A LIMB" and to Israel Patent Application serial number 160214 filed on 4 Feb., 2004 titled "A PORTABLE DEVICE FOR THE ENHANCEMENT OF CIRCULATION OF BLOOD AND LYMPH FLOW IN A LIMB" and to co-pending U.S. patent application Designated Ser. No. 10/469,685 titled "A PORTABLE DEVICE FOR THE ENHANCEMENT OF CIRCULATION AND FOR THE PREVENTION OF STASIS RELATED DVT" and filed 3 Sep. 2003 with priority dated 5 Mar. 2001, concurrently filed Israel patent application having a filing date of 26, Sep., 2004 and serial number not yet assigned and titled A PORTABLE DEVICE FOR THE ENHANCEMENT OF CIRCULATION, the content of which is incorporated herein by reference, which are incorporated herein by reference.

BACKGROUND OF THE INVENTION

1. Field of the Invention

The present invention generally relates to enhancement of blood or lymph flow in general, and to a portable pneumatic self-contained device for applying intermittent pressure on a body part in particular.

2. Discussion of the Related Art

Peripheral vascular disorders include venous, arterial or combined arteriovenous disorders. Venous thrombosis may seriously affect superficial or deep veins. Over time, serious conditions may develop to include edema, pain, stasis pigmentation, dermatitis, ulceration and the like. Serious cases of venous thrombosis may lead to phlegmasia cerulea dolens in which the extremities of the patient turns blue and may lead to gangrene and death. Various other ailments and conditions are likely to result from complications of venous thrombosis.

It is thought that most venous thrombosis occurrences begin in the valve cusps of deep calf veins. Tissue thromboplastin is released, forming thrombin and fibrin that trap RBCs and propagate proximally as a red or fibrin thrombus, which is the predominant morphologic venous lesion. Anticoagulant drugs such as heparin, the coumarin compounds, can prevent thrombosis from forming or extending. Antiplatelet drugs, despite intensive study, have not proved effective for prevention of venous thrombosis. Symptoms can appear within hours or sometimes longer. Other related venous conditions are varicose veins associated with valvular dysfunction causing aching, fatigue, and in some case subcutaneous induration and ulceration, superficial thrombophlebitis and even pulmonary embolism.

Arterial vascular disorders such as peripheral arterial occlusion may result in acute ischemia manifested in cold, painful and discolored extremities. In acute cases, the locations distal to the obstruction will be absent of pulse. Chronic occlusion will be manifested in the patient being able to walk to a lesser distance as the diseases progresses, causing unrelenting pain to the extremities, compromising tissue viability and leading to gangrene.

Increasing the flow of blood or lymph in the limb during periods of immobility is already a proven method to prevent the formation of DVT in the limb and to ease the suffering of peripheral vascular disorders. It secondarily prevents the formation of pulmonary embolism that commonly originates from such disorders. Increasing the venous return and arterial flow can also prevent formation of edema, pain and discomfort in the limb during periods of immobilization and assist in the prevention of arterial stenosis and occlusion.

Reduced circulation through a limb can also be observed in conditions affecting the arterial system such as in diabetes mellitus. It is believed that various vascular alterations such as accelerated atherosclerosis, where the arterial walls become thickened and loss their elasticity, diabetic microangiopathy, affecting capillaries, as well as neuropathy (loss and dysfunction of nerves) are responsible for the impaired circulation in the diabetic limb. The reduced blood supply to the limb entails stasis and ischemia in the distal limb. This ischemia leads to tissue death (necrosis) and secondary infections and inflammations. In addition, lack of cutaneus sensation caused by the loss of sensory nerves due to the diabetic neuropathy prevents the patient from being alert to the above-mentioned condition developing.

Enhancing circulation in general and prevention of stasis related disorders in particular, is achieved via non-portable large and cumbersome devices. Most of these devices can be used only by trained medical staff. Other methods of treatment suggest the use of worm compresses and medication.

Accordingly it is the object of the present invention to provide intermittent compression device for the enhancement of blood and lymph flow in a limb which is portable, self-contained and easily carried, small and lightweight, is easy to manufacture and is low cost. Such device will have enhanced energetic abilities enabling the efficient suction of blood and lymph though the arterial vessels. A further object of the invention is to provide such a device which provides intermittent compression using a fast and small pneumatic device, alternatively, combining the pneumatic and mechanical devices using low energy that does not involve tubing. It is a further object of the present invention to provide such a device which is simple to operate by a lay person without any special training in the field of medicine, is easily strapped over or attached to a limb and can be easily adjusted to fit persons of any size. Yet a further object of the invention is to provide such a device which allows for fast transitions from compressed to relaxed states and vice versa and which can exerts momentarily high forces by employing economic energy management.

Other advantages of the invention will be apparent from the description that follows.

SUMMARY OF THE PRESENT INVENTION

In accordance with the above objects, the present invention provides a device and method for enhancing and/or modulating blood and/or lymph flow in a body by applying periodic squeezing forces on a limb.

Preferably the device of the present invention is a small, portable, simple, device that produces intermittent mechanical compression of the venous or arterial system in a limb.

In accordance with one aspect of the present invention there is provided a portable device for modulating blood or lymph fluids or enhancing circulation in the body by generating intermittent squeezing forces on a limb, the device comprising an actuating member having a proximal face and a distal face; one or more adjustable strap or flap connectable to the lateral ends of a rigid member for encircling the limb; and said actuating member provides controlled periodical change in volume of said actuating member such that the distal face of the actuating member moves relative to the position of the limb; thereby applying intermittent squeezing forces on the limb and modulating blood or lymph flow within said limb. The actuating member is applying squeezing force to the limb and preferably it is an inflatable or deflate able cell that can receive fluid. The inflatable cell intermittently shorten and lengthen the circumference around the limb, thus providing cyclic transitions between a low-pressure relaxation phase and a high-pressure compression phase or high-pressure compression phase and a low-pressure relaxation phase The deflation of the cell generates a suction effect assisting in blood or lymph flow within the body. The inflation of the fluid cell generates pressure on the limb assisting in blood or lymph flow within the body. The deflating of said fluid is performed abruptly or quickly thus providing a suction effect. The deflation or inflation can be performed slowly. The suction effect comprises the generation of low pressure in the area proximal to a compression location and abruptly releasing said compression by releasing a strap or a flap or deflating the fluid cell. The device further comprising a rigid member juxtaposed with the distal face of the fluid-cell, the rigid member is having two lateral sides. The rigid member which can be a housing is preferably applied to the limb. The device further comprising a power source for supplying energy to said device. The power source is an fluid compressor or a fluid pump. Alternatively, the power source is a motor for providing energy to an at least one fluid compressor. The device further comprises a controller for controlling the operation of the actuating member. The controller is a frequency regulator for the controlling of the frequency of the inflation deflation cycle, or a central processing unit attached to frequency regulator for the controlling of the frequency of the inflation deflation cycle. Alternatively, the controller is a mechanical controller. The actuating member can include one or more chambers, be rigid, or semi-rigid or flexible, the chambers can be elastic. The device further comprises one or more valves for controlling fluid flow; one or more motor, one or more chambers and one or more cams. The strap comprises can comprise an inflatable fluid-cell. The device can also comprises a digital user interface, which is positioned juxtaposed to the device, or remotely from the device. The device further comprises a pivot, two cogwheels and a spring. The strap or flap can have the following versions: varying width comprising one or more strips; have at least one end thereof free to move around a corresponding connector such that the strap can be pulled by said end for tightening the strap around said limb; anchored in the appropriate position by fastening means; connected to an actuating device for pulling and releasing said at least one strap or flap thereby changing the circumference of limb. The cell can be disposable or replaceable. The further comprises a reservoir chamber for holding fluid to be provided to the actuating member and a piston, said chamber comprises one or more chambers and an energy charged element, such as a spring. The reservoir chamber can be a tank of constant volume. The device can also comprise a pressure gauge, a pressure sensor, or vacuum chamber for providing fast transition between inflated and deflated states of said actuating member. The device can also comprise a vacuum pump to evacuate fluid from said vacuum chamber thus creating substantially a vacuum in said chamber; and one or more valves for opening a conduit between said actuating member and said vacuum chamber, wherein fluid within said actuating member abruptly exists said actuating member and enters the vacuum chamber, whereby actuating member is deflated abruptly. The position of each valve can be determined by a controller.

In accordance with a second aspect of the present invention there is provided a portable device for modulating blood or lymph fluids or enhancing circulation in the body by generating intermittent squeezing forces on a limb, the device comprising a first actuating member having a proximal face and a distal face; said first actuating member provides controlled periodical change in volume of said actuating member such that the distal face of the actuating member moves relative to the position of the limb; and a second actuator having a rolling motivation connected to at least one adjustable strap or flap connectable to the lateral ends of a rigid member for encircling the limb and for providing periodical movement such that the strap or flap is intermittently pulled in and out of said rolling actuator; thereby applying intermittent squeezing forces on the limb and modulating blood or lymph flow within said limb. The device can further comprise a clutch for preventing said rotating actuator from releasing the at least one strap of flap. The releasing of the clutch will provide an abrupt motion of release of straps around limb, thereby creating a suction effect in the limb.

In accordance with a third aspect of the invention there is provided a device for modulating and/or enhancing blood and/or lymph flow in the body by generating intermittent squeezing forces on a limb. The device comprises an inflatable cell, at least one fastening element for fastening the inflatable cell to the limb and an actuator for intermittently inflating and deflating the inflatable cell. The inflatable cell is dimensioned so as to be in contact with only a section of the limb circumference. The actuator, comprising a mechanism for inflating/deflating the cell and a power source for supplying power to said mechanism, may be mounted on the limb adjacent to the inflatable cell. Alternatively, the actuator may be mounted on a body part other than the limb or may be located remotely from the user body.

In accordance with a fourth aspect of the present invention there is provided a method for modulating blood or lymph fluids or enhancing circulation in the body by generating intermittent squeezing forces on a limb, the method comprising the steps of actuating an actuating member having a proximal face and a distal face; encircling a limb with at least one adjustable strap or flap connectable to the lateral ends of a rigid member; and providing controlled periodical change in volume of said actuating member such that the distal face of the actuating member moves relative to the position of the limb; thereby applying intermittent squeezing forces on the limb and modulating blood or lymph flow within said limb. The actuating member is an at least one inflatable cell. The cell is inflatable or deflate able and can receive fluid. The method may further comprise the step of intermittently shortening and lengthening the circumference around the limb, thus providing cyclic transitions between a low-pressure relaxation phase and a high-pressure compression phase or high-pressure compression phase and a low-pressure relaxation phase. The method further comprises the step of generating a suction effect assisting in blood or lymph flow within the body. The deflating of said fluid is performed abruptly. The step of generating a suction effect comprises the steps of generation of low pressure in the area proximal to a compression location and abruptly releasing said compression by releasing a strap or a flap or deflating the fluid cell. The method further comprises the step of applying the device to a limb, the step of supplying energy to the device, and the step of controlling the operation of the actuating member. The step of controlling further comprises the step of regulating the frequency of the inflation deflation cycle. The method further comprises the step of opening or closing at least one valve for controlling fluid flow; the step of controlling the fluid flow through an at least one valve and the step of actuating the at least one strap or flap. The step of actuating comprises the step of pulling and releasing said at least one strap or flap thereby changing the circumference of limb. The method further comprises the step for holding fluid to be provided to the actuating member within a reservoir chamber; the step of driving a piston within said reservoir chamber so to inflate or deflate the cell and the step of charging an energy element within said reservoir chamber. Preferably, the energy element is a spring. The method further comprises the step of evacuating fluid from a vacuum chamber using a vacuum pump thus creating substantially a vacuum in said chamber and the step of opening a conduit between said actuating member and said vacuum chamber, wherein fluid within said actuating member abruptly exists said actuating member and enters the vacuum chamber, whereby actuating member is deflated abruptly.

BRIEF DESCRIPTION OF THE DRAWINGS

These and other features, aspects and advantages of the present invention will become better understood with regard to the following description, appended claims and accompanying drawings, showing embodiments of the invention where:

FIGS. 9A, 9B, 9C, 9D and 9E depict another mechanism in accordance with the present invention.

DETAILED DESCRIPTION OF PREFERRED EMBODIMENTS

Figure 1:
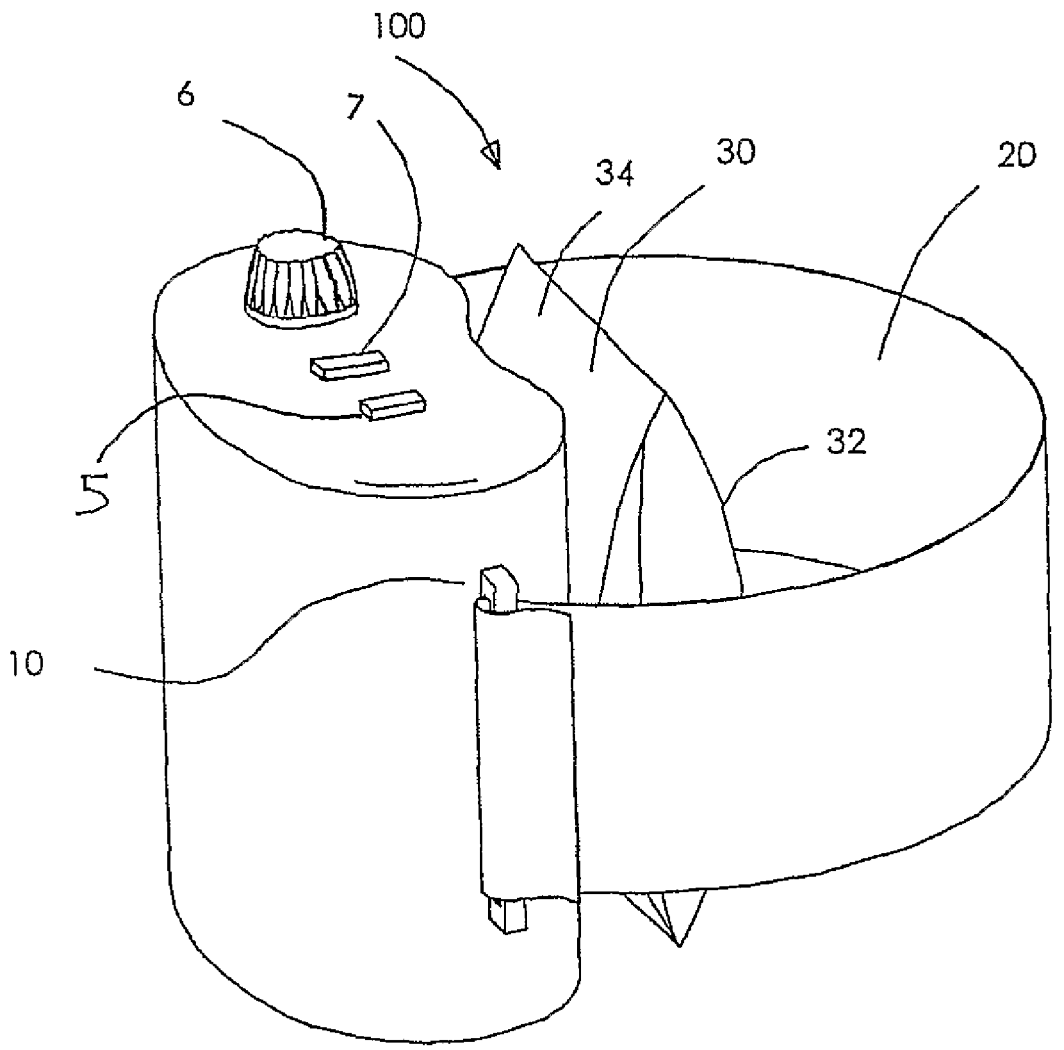
FIG. 1 is a pictorial illustration of a device in accordance with a preferred embodiment of the present invention.

The present invention discloses a portable device for enhancing circulation in a limb by applying intermittent squeezing force on the limb in a unique manner so as to obtain an energetic profile of operation allowing the device to assist in the return flow of venous blood and lymph fluids within the human body. The same principles can be applied so as to assist in the arterial flow of blood through the extremities of the body. The device according to the invention can be used for intermittent compression of the extremities and for the enhancement of circulation in a limb. The device is portable, self-contained and easily carried and can be helpful for enhancing venous, arterial and lymph flow. The device can be used for improving the general circulation in a limb during periods of immobility for the prevention of stasis related disorders such as DVT, edema and lymphedema, and other peripheral vascular disorders as well as for conditions of reduced circulation such as in diabetic patients, post surgical patients, heart disease patients and the like. As noted above, the device and method of the present invention provides a suction effect within the veins. The auction effect is caused by the use of energetic profiles associated with the operation of the device of the present invention. The release of pressure previously applied to the limb results in a suction effect on the venous return of blood and lymph flow. Likewise, the controlled application of pressure on the limb provides a relatively strong blood flow to areas that were previously deprived of blood flow subject to the compression state of said limb, enhancing the arterial flow of blood in the extremities. Another benefit of the application of controlled pressure on the limb results in providing the extremities with intermittent in force blood flow that can assist the user's extremities blood vessels in the release of blockages existing within the capillaries or larger blood vessels. The changes in compression can be moderate or abrupt to suit the effect desired. In the venous blood vessels and the lymphatic system abrupt changes in the compression applied to the limb will cause a suction effect discussed above enhancing the flow of blood and lymph fluids. In the arterial blood vessels the gradual application of pressure on the limb will enhance the flow of blood towards the extremities. As noted above, the suction effect also aid for overcoming vascular blockage disorders. Thus, the suction effect can assist patients suffering from vascular blockage disorders in the opening and releasing at least part of said vascular blockages. The device design discloses favorable energetic features, allowing the operation of the device at a maximum output with minimal energy input. In one preferred embodiment of the present invention, the device comprises at least one squeezing force actuating member, a rigid member juxtaposed having two lateral sides, at least one adjustable strap connectable to at least one of the lateral ends of the rigid member for encircling the limb, and a mechanism for intermittently squeezing said limb. The actuating member is associated with the at least one of the lateral ends that is connected to the at least one adjustable strap. In another embodiment the actuator provides power to a mechanism for inflating or deflating a cell, said cell is preferably a fluid cell to provide intermittent compression to a limb. Said cell can also provide a leverage to a stationary flap or strap which provide intermittent compression to a limb. The flap or strap can be connected to an actuator which changes the circumference of the limb while the fluid cell is inflating or deflating thus providing a device having two actuator for providing intermittent compression to the limb. A person skilled in the art will readily appreciate that the present invention can be used for the enhancement of both arterial and venous blood and lymph flow in a limb (upper and lower).

Figure 2:
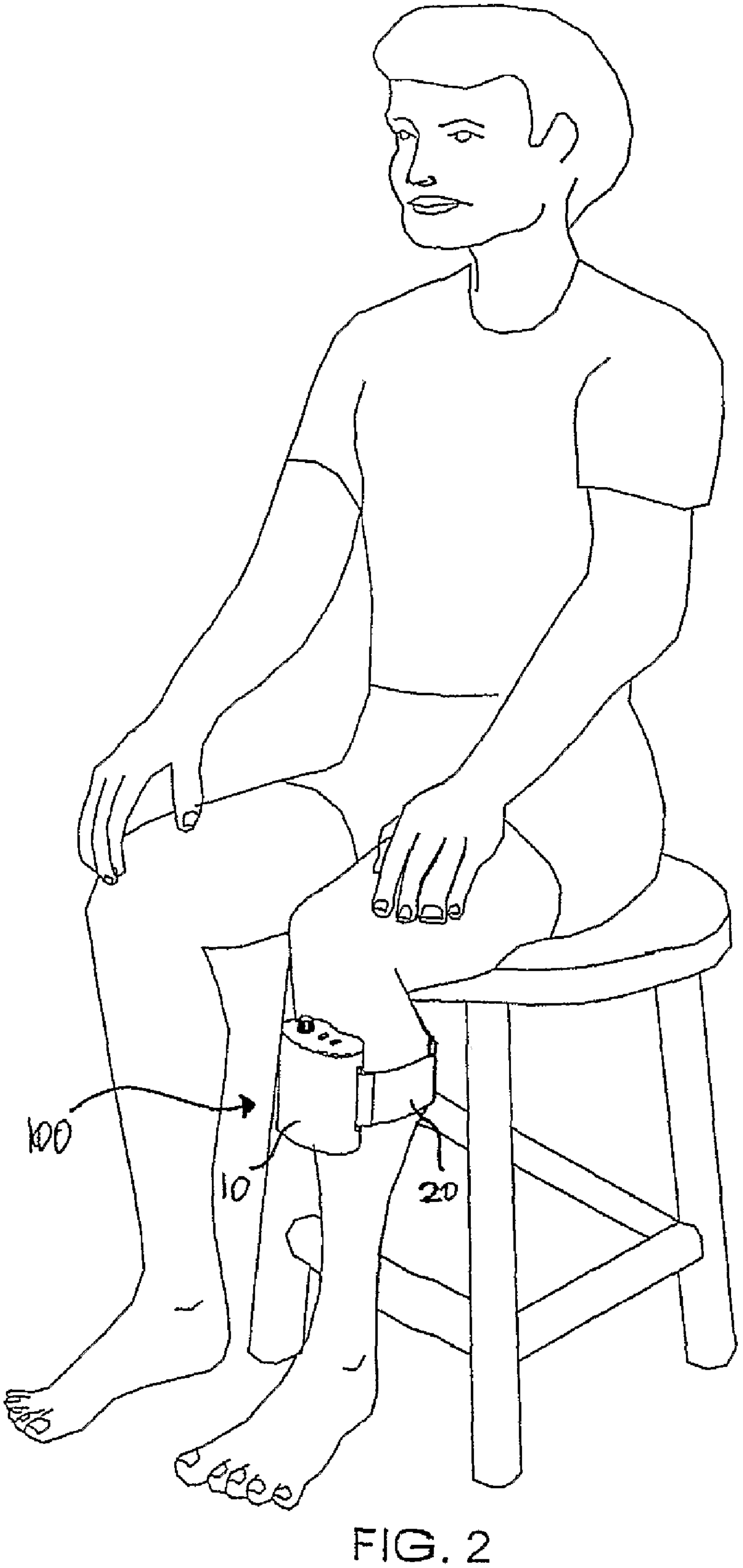
FIG. 2 is a pictorial illustration of a device of the present invention worn by a user.

Turning now to the Figures, FIG. 1 shows a preferred embodiment of the portable device of the present invention, generally designated 100. FIG. 2 shows the same worn on the calf of a sitting person. Device 100 can be worn directly on the bare limb, or on a garment, such as trousers, worn by the person using the device. Device 100 comprises a housing 10 attachable to limb by a strap 20 and an inflatable cell 30 interposed between housing 10 and the limb. Inflatable cell 30 is an actuating member that applies a squeezing force to the limb. During operation cell 30 is intermittently inflated and deflated with fluid to intermittently shorten and lengthen the circumference around the limb, thus providing controlled periodical change through the change of volume of the actuator. The change in volume of the actuating member results in the movement of the distal face of said actuating member relative to the position of the limb. The actuating member change of volume provides for cyclic transitions between a low-pressure relaxation phase and a high-pressure compression phase or high-pressure compression phase and then low-pressure relaxation phase. Each phase can be the long or the short end associated with each transition. For example in the preferred embodiment of the present invention applying a long high-pressure compression phase and a short term low-pressure phase the transition between the phases is abrupt will cause a suction effect. The word abrupt is used to describe a rapid transition term between the high pressure compression term and the low pressure compression term and vice versa. The abrupt transition can be equal or of less than 400 miliseconds. The abrupt transition is achieved by applying minimal energy resources, thus rather small overshooting, if any, of access pressure within inflatable cell is required for reaching the required squeezing and relaxation of a limb during the intermittent squeezing. In accordance with the preferred embodiment shown in FIG. 1, housing 10 and cell 30 are configured to be placed against the bone while strap 20 is wrapped around the muscles tissue, such that when cell 30 is inflated, strap 20 is stretched and pressed against the muscles. The preferred embodiment may be construed without a housing, rather with a rigid member which will provide support for the straps or flaps which may be replaceable or disposable. Such an arrangement allows for applying uniform radial squeezing forces on the muscles while keeping the volume of cell 30 relatively small. A small volume of cell 30 allows, in its turn, the use of a relatively small, light-weight energy supplying mechanism such as pump or fluid compressor to inflate the cell as well as facilitating rapid transition between relaxed to compressed states. However, it will be easily realized that according to another embodiment of the invention, the housing 10 and the cell 30 can be placed against the muscles, such that the pressure on the muscles is directly applied by the cell 30. In yet another embodiment of the present invention the device does not comprise housing. If a housing is used, the housing 10 can comprise the mechanism responsible for the intermittent inflation/deflation of cell 30 coupled to cell 30 by means of a short tube (not shown) extending through an opening in the inner wall of housing 10. The device can be preferably designed to operate using a fluid such as air. In alternative embodiments other like fluids can be used to inflate or deflate or change the volume within said cell. In yet another alternative of the present invention a liquid can be used to change the volume of cell 30 such that intermittent compression is attained according to the principles of the invention. In the description below the use of air as an example to the fluid used in association with the devices described herein should not be construed to limit the invention rather to provide an example of a fluid that can be used to make and use the invention. The power supply for the device may be of the internal power supply type such as a rechargeable or non rechargeable low voltage DC batteries or an external power supply type such as an external power outlet connected via an AC/DC transformer such as a 3-12V 1 Amp transformer, fed through electrical wires to a receptacle socket in the device (not shown). The device may be provided with an on/off switch 5, a pressure regulator 6 for regulating the pressure exerted on the limb during the compression phase and a frequency regulator 7 for regulating the frequency of the inflation/deflation cycle. Alternatively, the device may be provided with an optional digital or analog user interface juxtaposed for presetting the operational parameters of the device 100. According to a further embodiment the digital or analog user interface can be positioned remotely to device 100. Hence, the operational parameters data can be transmitted to the remote location by a communication cable connected or by an RF transmitter positioned within device 100. The operational parameters may include cycle frequency, relaxation and compression phase durations, pretension pressure value during the relaxation phase and pressure value at the compression phase. In the preferred embodiment of the present invention, strap 20 is connectable to opposite sides of housing 10 or the mechanism itself. Strap 20 can be of a constant or varying width, comprised of one or more strips of fabric or like strong but flexible material. Strap 20 is adjustable and can be adjusted to fit the size of the limb and the location at which the device is worn on the limb. The strap may be one strap having at least one of its ends free to move through its corresponding connector such that the strap can be pulled by said end for tightening the strap around said limb. Said end is then anchored in the appropriate position by fastening means such as a hook or loop strips, snap fasteners, latch or any other fastening means. The second end of strap 1 can be connected to its corresponding connector either in a permanent manner or can be also movable allowing both ends to be pulled and anchored simultaneously for better fitting. Yet, in accordance with another embodiment of the invention, one end of the strip is secured to an actuating device such as a retracting mechanism (not shown) positioned at one side of housing 10 while the second free end is provided with either one of the aforementioned fastening means or by means of a quick connector. Alternatively, strap 20 can comprise two portions, each having one end permanently connected to one end of housing 10 or to components within and its other free end provided with means to connect to the free end of the other portion. In such case the strap 20 can be pulled outwardly and inwardly with respect to said device thus enabling intermittent compression of the limb both by cell 30 and one or more straps 20. In such case, both ends of the strap are connected to an actuating member which can be a retracting and releasing mechanism as is described in co-pending U.S. patent application Designated Ser. No. 10/469,685 titled "A PORTABLE DEVICE FOR THE ENHANCEMENT OF CIRCULATION AND FOR THE PREVENTION OF STASIS RELATED DVT" and filed 3 Sep. 2003 with priority dated 5 Mar. 2001, the content of which is incorporated herein by reference. In yet another alternative embodiment the device 100 comprises one or flaps instead of straps. Such flaps and their manner of operation are further described in detail in concurrently filed Israel patent application having a filing date of 26, Sep., 2004 the serial number not yet assigned and titled A PORTABLE DEVICE FOR THE ENHANCEMENT OF CIRCULATION the content of which is hereby incorporated by reference. In the context of the present invention any reference to one or more straps attached to the device 100 or like devices described herein below or mechanisms associated therewith should also be construed as reference to one or more flaps as they are described in detail in the application incorporated above by reference.

Cell 30 is having a proximal face 32 in contact with the limb when device 10 is worn around the limb or attached to the limb, and an opposite distal face 34 in contact with the inner face of housing 10. Cell 30 is made of pliable fluid-impermeable material and is preferably filled with compressible, resilient porous filler for reinforcing the cell, for reducing the volume of fluid required to inflate or fill the cell and for cushioning the contact with the limb. Cell 30 can comprise any shape and size sufficient to inflate and deflate or fill and evacuate said cell such that the circumference juxtaposed between cell 30 and strap 20 or flaps, if such are used, is reduced so as to provide intermittent compression of the limb. The preferred shape will be that of the limb to which the device is applied and likewise the preferred size will depend on the size of the limb to which the device is applied. The cell 30 can be disposable or replaceable such that the same device can be used for the treatment of various users by replacing the cell 30 after each use or after pre determined number of uses. To be replaceable the cell 30 will also comprise an interface to rigid member or housing 10, which may optionally also include an interface to tube 66. Such interface can for one non-limiting example comprise of a cell having an attaching means such as Velcro or like hooks and pins connection and a plastic tube adapter to connect both the cell 30 to housing 10 or rigid member and to tube 66 by means of the plastic tube adapter. The intermittent compression of the limb allows the limitation, restriction or the enhancement of flow of blood and lymph within said limb. When the intermittent compression is controlled as provided herein, a suction effect is created in the venous and lymphatic system enabling an enhanced blood and lymph return within said system. A short tube (not seen in FIG. 1) connects between cell 30 and the mechanism encased in housing 10 for transferring in and out of cell 30 a fluid allowing the inflation or deflation of said cell. It should be emphasized that the length of the tube is kept to minimum such that practically cell 30 is directly connected to housing 10 with no external tubing. In an alternative embodiment cell 30 is connected directly to a port or an opening within the fluid reservoir. If housing 10 is not present then cell 30 is attached to the mechanism as described further below for inflating and deflating said cell. This enhances rapid inflation of the cell by eliminating dead volume due to tubing. It also enhances the compactness of the device and eliminates the possibility of blockage of fluid passage by tubing entanglement or bending.

Figure 3A:
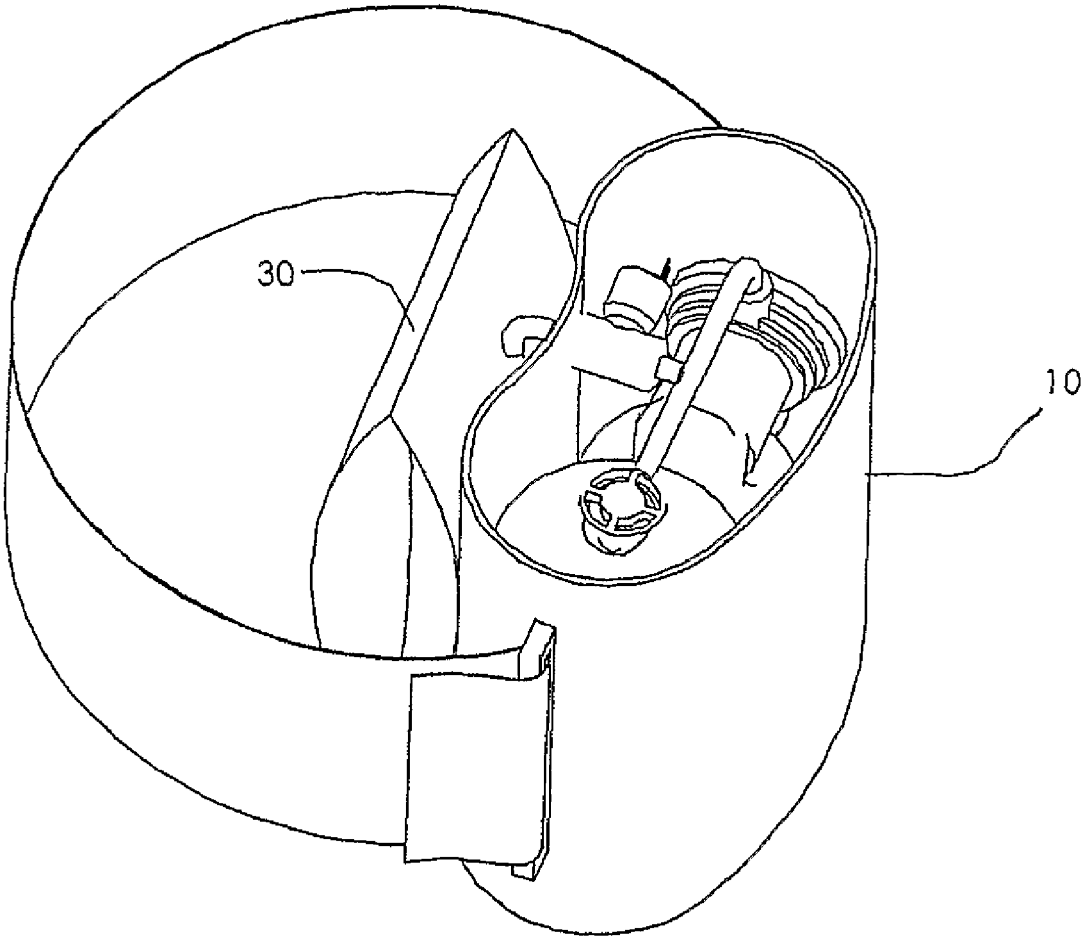
FIGS. 3A and 3B are a top perspective view of one embodiment of the device of the invention with top cover removed and housing removed, respectively.
Figure 3B:
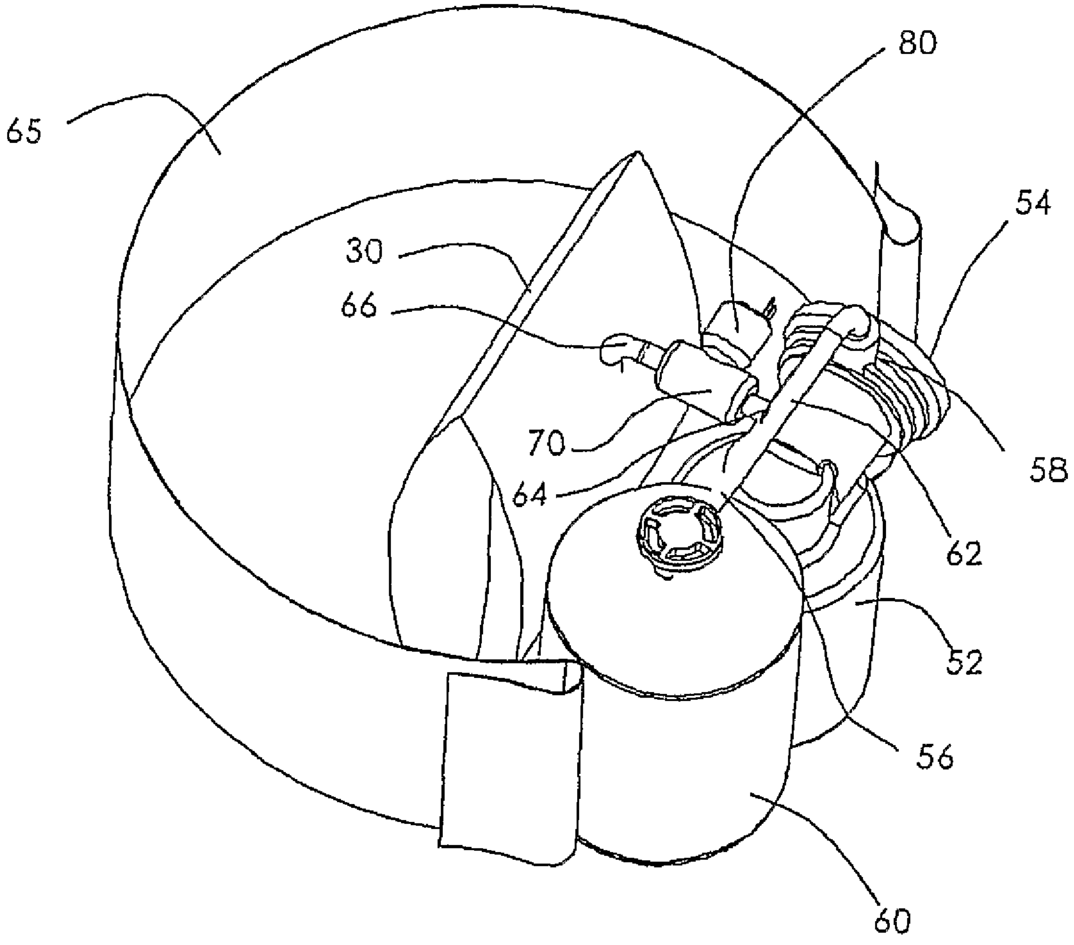

Referring now to FIGS. 3A and 3B, there is shown a mechanism for intermittent compression of a limb in accordance with a first embodiment of the invention. FIG. 3A illustrates the mechanism compactly packed in housing 10 with the upper cover of the housing removed. FIG. 3B illustrates the mechanism only. In the examples below air serves as the fluid to be used in association with the inflation or deflation of cell 30. For the purpose of clarity housing 10 is shown to comprise the mechanism operating said device. Persons skilled in the art will readily appreciate that the device can be manufactured and used without said housing. In accordance with this embodiment, the mechanism comprises a motor 52, one or more straps 65, a mini-air compressor 54, preferably miniaturized, an air reservoir chamber 60 to hold the air or other fluid suitable for inflating and deflating cell 30, interposed between compressor 54 outlet and cell 30 inlet, a bi-directional valve 70 located at the inlet of cell 30 and a controller 80 for controlling the device operation. It will be realized that motor 52 and mini compressor 54 may comprise one unit, for example. Bi-directional valve 70 can be opened to connect cell 30 to chamber 60 or to ambient atmosphere. When closed, valve 70 isolates cell 30 from both chamber 60 and the atmosphere. During operation, valve 70, controlled by controller 80, is alternately switched between its three states to alternately inflating/deflating cell 30, thereby effectuating transitions between relaxed and compressed states of cell 30. Controller 80 can be a mechanical controller comprising cog wheels (not shown), at least one spring (not shown) which can be wound and charged and an shaft connected to valve 70 (not shown) to open and close said valve. When said charged spring is released, said cog wheels turn and in turn move said shaft so as to intermittently change valve 70 position from an open to a closed position. In accordance with this embodiment the user will wind a handle (not shown) to charge said spring, or the device will be supplied with a charged spring, which in turn when released turns said cog wheels and shaft associated with said valve 70 operating as a mechanical timing mechanism allowing the intermittent release of fluid into cell 30 and in addition the opening of a release valve, if present. In accordance with this embodiment the operation of valve 70 is time dependant. Other like mechanical timing mechanisms can be used to operate 70. Controller 80 can alternatively comprise a central processing unit (CPU) or a mechanical mechanism activated by a pressure gauge (not shown) positioned by cell 30. In accordance with this embodiment the CPU receives continuous data input from said pressure gauge which can be located within said cell 30 or within fluid reservoir 60 or within both. When sufficient fluid has entered cell 30 the CPU instructs valve 70 to close and in the opposite instance to close. In accordance with this embodiment the control of entry and exit of fluid to or from cell 30 is pressure dependant. In an alternative embodiment the CPU is replaced by a mechanical pressure measuring device which mechanically closes and opens valve 70 based on the pressure measured within either cell 30, reservoir 60 or both. Controller 80 can further be connected to a controller either mechanical or electrical controlling the performance of motor 52 and compressor 54 to regulate the compression of air in reservoir 60, and operation of compressor 54. It will be realized that valve 70 may be replaced by two separate valves, one for opening/shutting the passage between chamber 60 and air-cell 30 for inflating the cell and another one for opening/shutting the passage between cell 30 and atmosphere for deflating the cell. If other fluid rather than air is used and the fluid should not be released into the atmosphere, an additional collection reservoir (not shown) can be used. In such embodiment fluid exiting cell 30 will enter collection reservoir and can be pumped back into the reservoir 60 for additional use. In accordance with this embodiment the devices uses a close system which is can be friendlier to the environment when the use of some fluids is desired and also efficient because fluid will not be wasted through the use of the device. Valve 70 or if more than valve is used can be mechanical, electric or pneumatic activated valves. In one embodiment controller 80 is connected to a CPU that in turns controls the working mode of motor 52 and compressor 54. CPU (not shown) can control the compressing and relaxation state as well as the transition rate between the two said states and the length between each state and of each state. In other embodiments of the present invention the entire mechanism is mechanically or pneumatically operated either by the force generated through the release of fluid into cell 30 or by use of the force of charged springs. In yet another alternative, the user can turn on and off a motor driven by a switch provided on the housing encasing the mechanism.

During operation, compressor 54, powered by motor 52, pumps ambient air into reservoir chamber 60. During the relaxation phase, valve 70 is closed allowing compressor 54 to build up a high pressure in chamber 60. It will be realized that the use of reservoir chamber 60 between compressor 54 and air cell 30 allows for the use of a relatively low rate compressor to charge chamber 60 gradually. Thus, depending on the air supply rate, compressor 54 may operate continuously or can be stopped when a predetermined pressure is reached within chamber 60. Accordingly, a pressure gauge or a pressure sensor can be placed within reservoir chamber 60. The pressure gauge or the pressure sensor can be connected to the CPU regulating the operational state of the inflating/deflating mechanism. In accordance with the embodiment depicted in FIGS. 3A, 3B, chamber 60 is a small rigid tank of constant volume. According to the invention compressor 54 is activated by motor 52. One example of motor with compressor can be model No. cc2300 which is a 12V cordless air compressor manufactured by Campbell Hausfeld. However, other compressors with motor which are substantially small in size and light in weight can be used. According to the invention conveying of air in and out of inflatable air cell 30 provides the intermitted compression and relaxation on limb surrounded by strap 65. Thus, the transition rate between compression and relaxation state is determined by the air-conveying rate in and out of air cell 30. Compressor 54 compresses air to reservoir chamber 60 during the relaxation state, thus, mounting a pressure within chamber 60. The air is conveyed from compressor outlet 58 through pipeline 62 into chamber outlet 56. During the relaxation state valve 70 controlled by controller 80 is closed and allows the pressure build up within chamber 60. During the compressed state controller 80 opens valve 70 rapidly, thus, providing passage of compressed air to inflatable air cell 30. Thus, the compressed air passage from chamber 60 to air cell 30 is rapid subject to the pressure difference between chamber 60 and air cell 30 and the opening of valve 70. During the compressed state of the inflating/deflating mechanism air is conveyed from chamber 60 through chamber outlet 56, pipelines 62, 64, open valve 70, and air cell outlet tube 66 into air cell 30. As a result of the inflation of air cell 30 the limb placed within strap 68 and air cell 30 is compressed subject to the perimeter reduction. The relaxation state comprises a first step of opening valve 70 to the atmosphere, thus, providing air within air cell 30 to exit through outlet 66 and valve 70. The second step comprises the closing of valve 70 and commencing of an air pressure build up within chamber 60 by compressor 54. According to other embodiments, the two steps of the relaxation state are preformed together, thus the air from air cell 30 is conveyed to atmosphere and the pressure build up within chamber 60 is performed concurrently. This embodiment will operate in a similar fashion by using more than one valve or alternatively by using a valve enabling such performance. The rate of the intermitted compression on the limb is subject to the pre-designated parameters set by the user. Thus, a user can set the frequency of the intermitted compressing by regulating the compressing air power performed by motor 52 and compressor 54 and the coordination of the opening and closing of valve 70 controlled by controller 80. Additionally, a user can set the compression reached in every intermitted compression by regulating the operational mode of compressor 54. One skilled in the art can easily comprehend that the size of air cell 30 in comparison to the size of housing and mechanism within is provided according to one aspect of the provided preferred of the present invention. Other sizes of air cells with other proportionality to a housing and mechanism can be provided as well according to the present invention.

Figure 4:
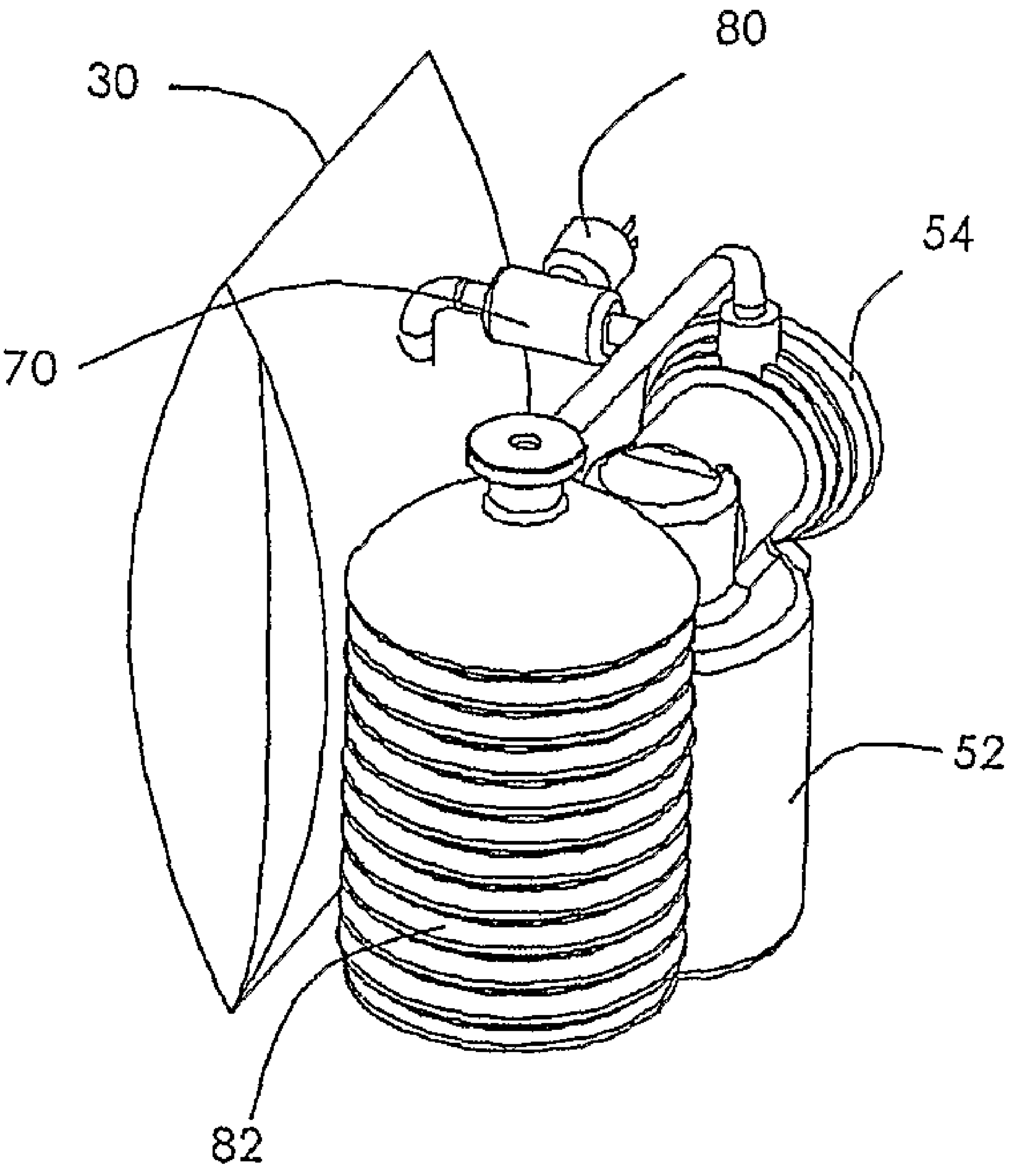
FIG. 4 depicts a mechanism in accordance with a second embodiment of the invention.
Figure 5A:
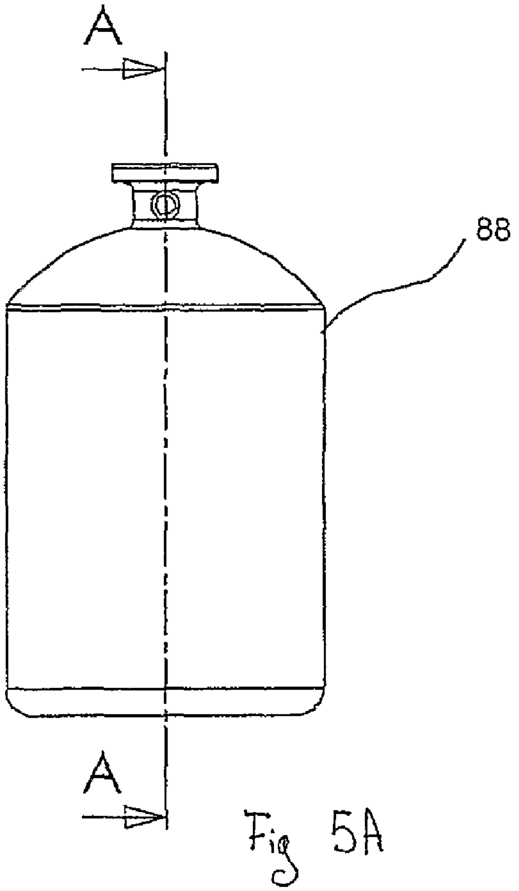
FIGS. 5A and 5B depict a pressure container side view and its longitude middle cross section, respectively, according to one preferred embodiment of the present invention.
Figure 5B:
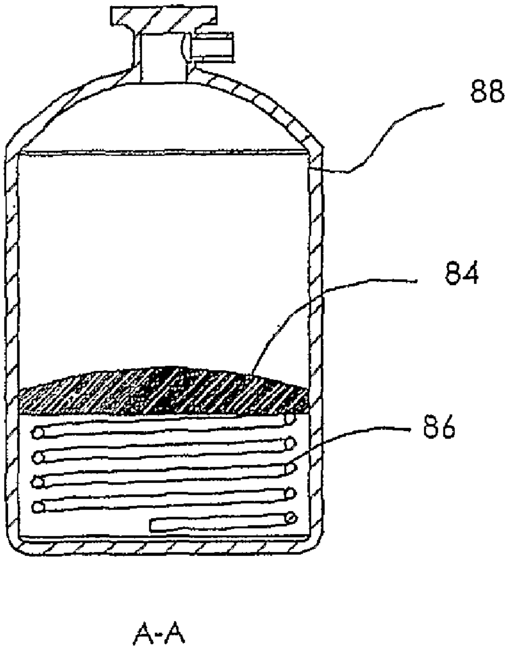

FIGS. 4, 5A, 5B present different reservoir chambers that further diminish and reduce the transition time from relaxed to compressed state. Accordingly, FIG. 4 presents an inflating and deflating mechanism of an inflatable air cell comprising substantially the same elements as the mechanism depicted in view of FIGS. 3A, 3B above. However, reservoir chamber 82 is an elastic chamber known also as a bellow type chamber. Thus, reservoir chamber 82 provides further springiness to the inflating and deflating mechanism to facilitate rapid inflation of inflatable air cell 30. According to other embodiments, reservoir may be an elastic container of a variable volume such as an elastic inflatable cell (e.g., a balloon) or other. FIG. 5A presents reservoir chamber 88 that can replace reservoir chamber 60 depicted in view of FIGS. 3A, 3B. Reservoir chamber 88 longitude cross section at line A-A is presented in FIG. 5. Reservoir chamber 88 comprises a movable piston 84 mounted on a compressible spring 86. Thus, in order to further reduce the inflation time of cell 30 and consequently reducing the transition time from relaxed to compressed states, chamber 82 is provided with a movable piston 84 mounted on a compressible spring 86 so that when air is forced into the chamber, the spring is loaded as well. Accordingly, when, valve 70 is opened to connect cell 30 and chamber 82, the spring facilitates the rapid inflation of the cell. In accordance with another embodiment, reservoir chamber 60 may be replaced with other types of reservoirs provided with such as an aerosol or like single or multi use or detachable or replaceable reservoirs.

Controller 80, responsible for timing the inflation/deflation cycle via valve 70 is preferably an electronic unit electrically coupled to the valve. However, controller 80 may be a mechanical timer such as for example a rotating cams shaft driven by the same motor that drives the air compressor where the cams mounted on the shaft are configured to open/shut the valve or valves to effectuate inflation/deflation of the cell at predetermined times.

Figure 6A:
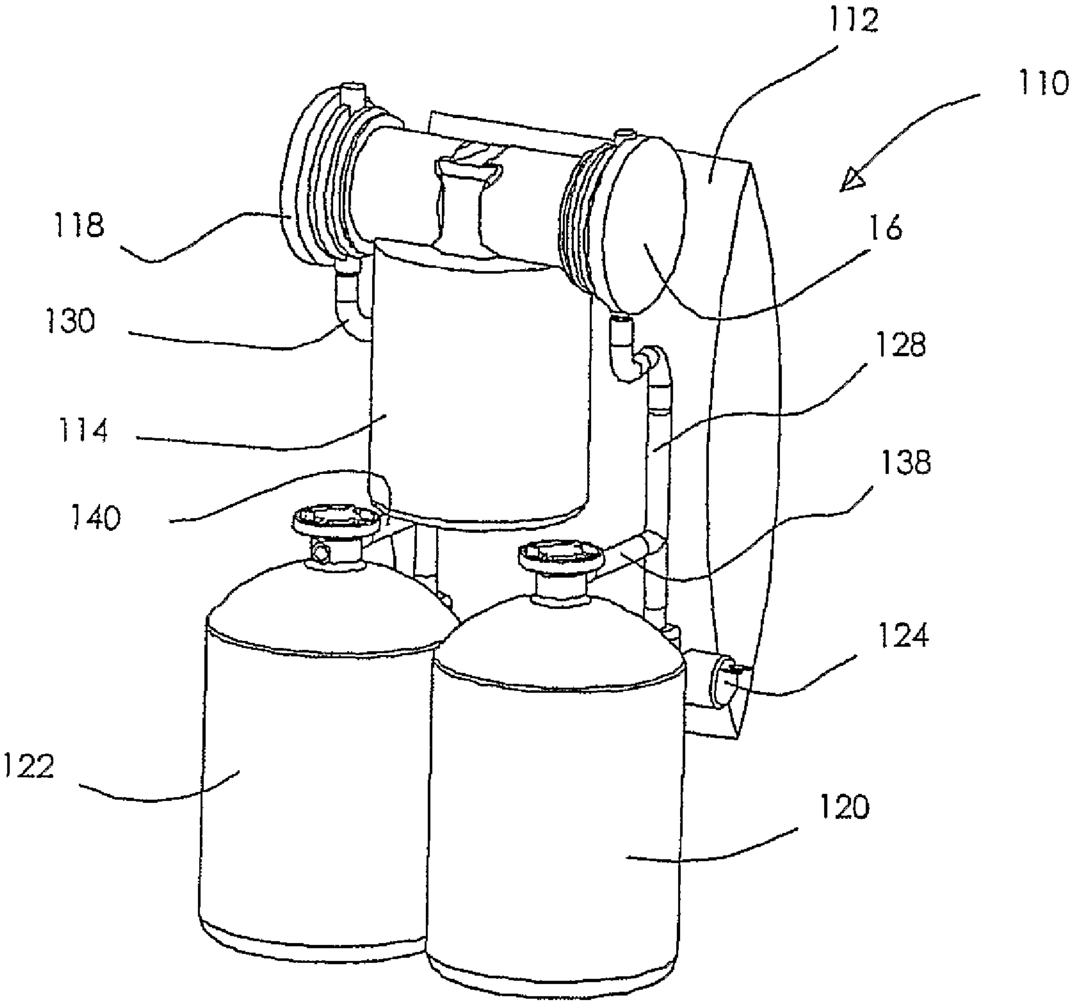
FIGS. 6A and 6B is a another mechanism in accordance with a the present invention.
Figure 6B:
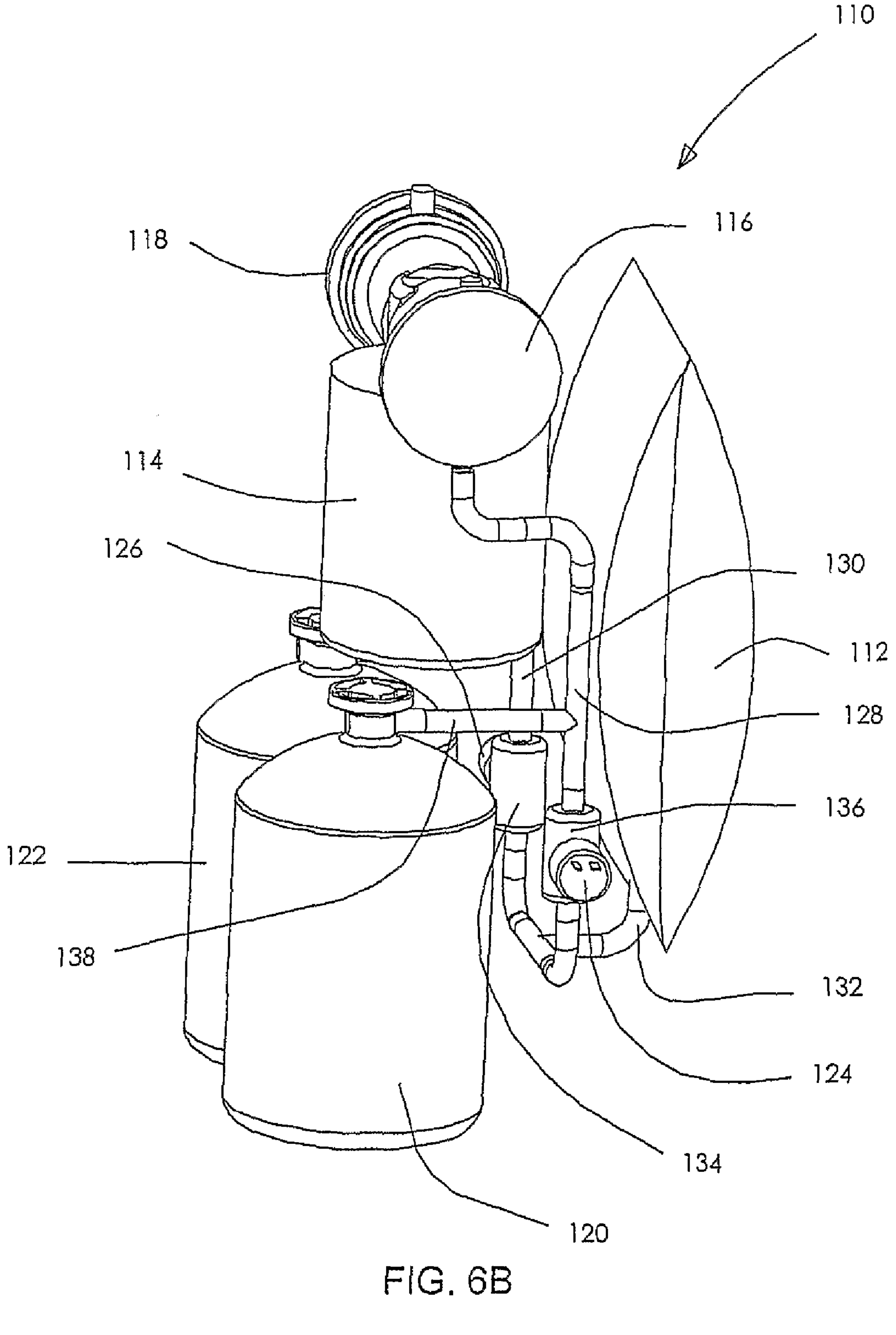

FIGS. 6A and 6B present another embodiment of an inflating and deflating mechanism used within a device placed on limb as depicted in view of FIGS. 1 and 2 above. Mechanism 110 according to the present invention can be placed within a housing such as depicted in view of FIGS. 1, 2. One skilled in the art can appreciate that other sizes and shapes for housing mechanism 110 such as longitude, oval and other shapes can be used as well. Mechanism 110 comprises an inflatable air cell 112, reservoir chamber 122, vacuum chamber 120, motor 114, compressor 118, and a vacuum pump 116. Reservoir chamber 122 and vacuum chamber 120 within mechanism 110 provide fast transitions between the inflated and deflated state of fluid or air cell 112 as will be depicted bellow. Reservoir chamber 122 can be from the type shown and depicted in view of FIGS. 3B, 4, 5B above or any other type of chamber that is light weight and can undertake pressure mounted by compressor 118. Vacuum chamber 120 can be substantially identical to the size of reservoir chamber 122. Nevertheless, vacuum chamber 120 inner volume is preferably substantially constant. The fabrication material of vacuum chamber 120 can be metal, polymers or plastic, or a combination thereof. Vacuum chamber 120 is sealed and can comprise insulation on the walls of the chamber. Vacuum chamber 120 can be smaller or larger than reservoir chamber 122. Motor 114 activates compressor 118 and vacuum pump 116. Mechanism 110 provides an embodiment wherein compressor 118 and vacuum pump 116 are positioned along one crank handle (not shown) activated with one motor 114. During the relaxation state of a device (not shown) as depicted in view of FIGS. 1, 2 above the inflatable air cell 112 is relaxed as well. Similarly, during the compressed state of a device air cell 112 is substantially filled with air. Pressured air within reservoir chamber 122 is exploited for providing rapid transition of air from reservoir chamber 122 to air cell 112. A rapid transition time from compressed state to relaxation state is reached by the vacuum build up within vacuum chamber 120. Accordingly, the pressure drop between the surplus compressed air within air cell 112 is conveyed to the vacuum chamber 120. The conveying of air in and out of reservoir chamber 122 and vacuum chamber 120 is by opening and closing of valves 136, 134, respectively. Valves 134, 136 can be valves having two positions, open and close, providing flow of air in and out of said chambers. Alternatively, valves 134, 136 can have three positions, providing open and closed positions, as within the former presented valves, and, an atmosphere opening as depicted in view of FIGS. 3A, 3B above. The positions of valves 134, 136 are controlled by controllers 124, 126, respectively. Controllers 124, 126 can comprise a CPU or, alternatively, connected to one or more CPU that regulates the position of valves 134, 136. During the transition from relaxation state to the compressed state valve 134 is set by controller 124 on its closed position and valve 136 is set by controller 126 on its open position. Accordingly, the compressed air within reservoir chamber 122 is conveyed through a conduit such as a pipeline 140, valve 136, pipeline 132 into air cell 112. Similarly, during the transition from compressed state to relaxation state of mechanism 110 valve 136 is set by controller 126 on its closed position and valve 134 is set by controller 124 on its open position. Accordingly, compressed air within air cell 112 is conveyed through pipeline 132, valve 134 to pipeline 138 and into vacuum chamber 120. The operation of mechanism 110 is controlled by control processing unit (CPU) that controls the operational mode of motor 114, compressor 118, vacuum pump 116 as well as the operation of valve controllers 124, 126. Compressor 118 and vacuum pump 116 can have a substantially alternately operational mode. Thus, pressure build up operation by compressor 118 within reservoir chamber 122 and vacuum build up operation by vacuum pump 116 within vacuum chamber 120 follow each other. Alternatively, the pressure build within reservoir chamber 122 and vacuum build up within vacuum chamber 122 have an overlapping or partially overlapping operational mode of compressor 118 and vacuum pump 116.

Figure 6C:
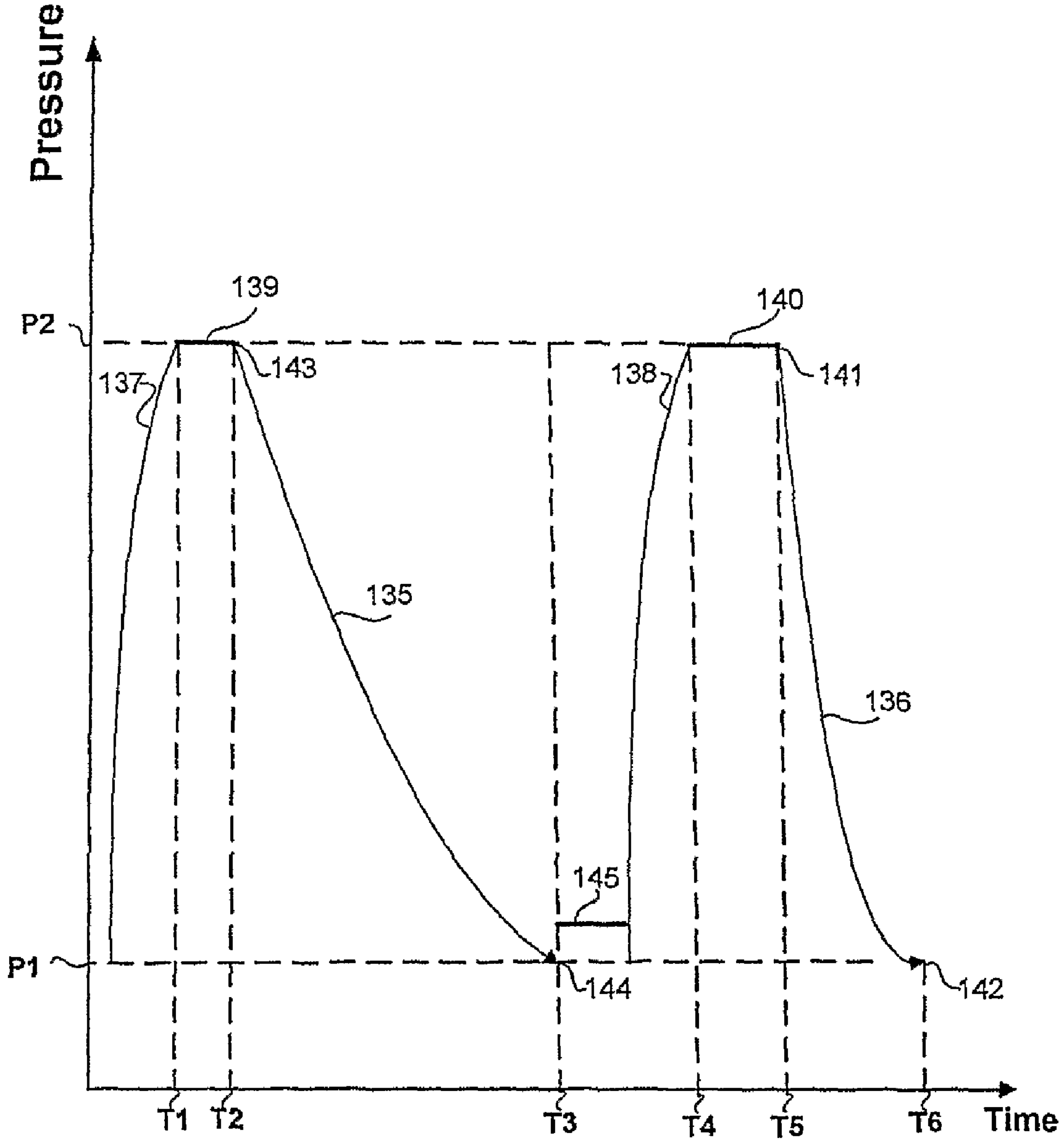
FIG. 6C provides a graph view of the characteristic suction effect created by the mechanism of the present invention, according to some preferred embodiment of the present invention.

The effect created by the operation of the devices depicted in the various embodiments of the present invention can be further understood from the graph shown in FIG. 6C. Said graph is showing the energy profile associated with the operation of the embodiments of the device of the present invention creating a suction effect in the venous system of the user of the device. The graph depicts the energetic profile of operation allowing the device to assist in the return flow of venous blood and lymph fluids within the human body. The graphs show the pressure applied to the limb of the user over time. The graphs depict the squeezing operation in a slow release mechanism and fast release mechanism. The slow release mechanism is depicted in view of slope 135 and the fast release mechanism is depicted in view of slope 136. Slope 135 provides a characteristic pressure decrease profile of a device applying pressure on a limb. Slope 136 provides a characteristic pressure decrease profile of a device applying pressure on a limb using a fast release mechanism as disclosed in the preferred embodiments of the present invention.

Figure 7C:
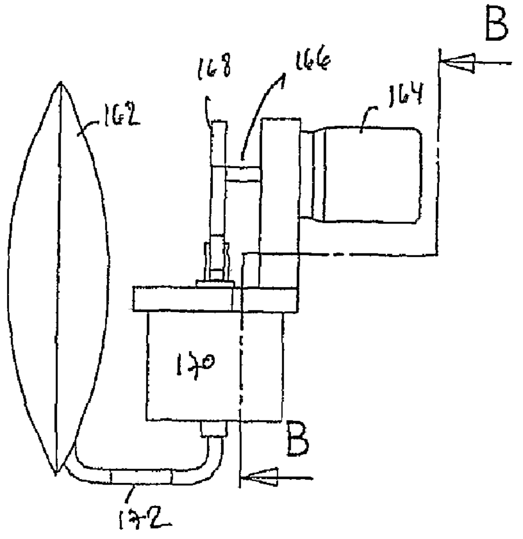
FIGS. 7A, 7B and 7C depict fast suction mechanism in accordance with one preferred embodiment of the present invention.
Figure 7B:
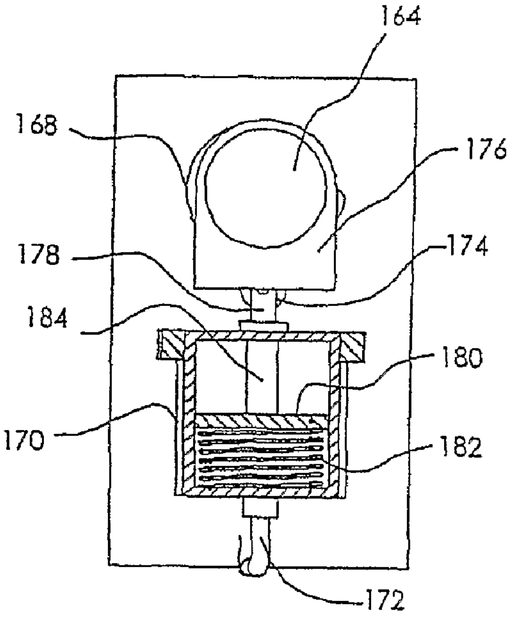
Figure 7A:
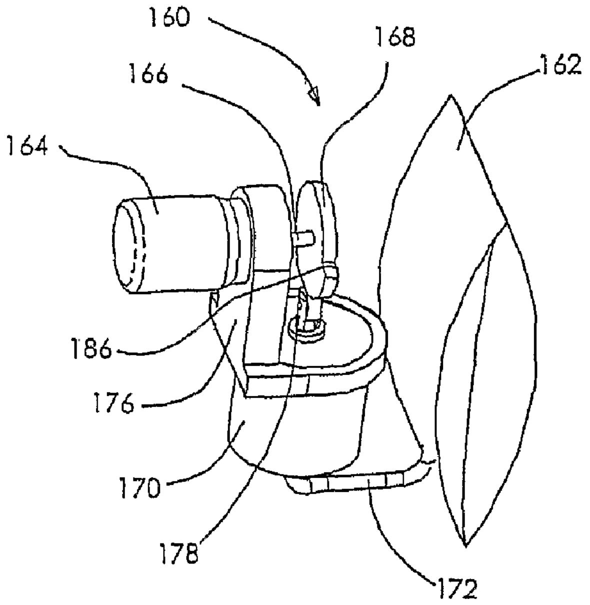

In the shown graph one version of compression of the limb is shown in view of slope 137, 138. Other versions of compression can also be used to obtain the same result of having a suction of the blood and/or lymph flow in the venous system. Thus, the compression used can be performed over a longer period of time or a shorter period of time and can apply more or less pressure. The compression periods of time from the end of the compressed state to the beginning of the relaxed state are shown in view of lines 139, 140. The compression period of time as is depicted in the length of lines 139, 140 can be variable and preferably from about one second to a about few minutes, The fast release mechanism shown in view of slopes 136, 138 and compression period 140 provides a relative shorter transition time from the end of the compressed state 141 to the end of the relaxed state 142 in comparison to the slow release mechanism shown in view of slopes 135, 137 and compression period 137 wherein the transition time from the end of the compressed state 143 to the end of the relaxed state 144 are relatively longer. In addition, the period of time between one cycle of compression (said one cycle comprising a compression slope, a compression period and a relaxation slope) to another such cycle of compression 145 can be short or long. Such period of time is designed to obtain a continuous suction effect described in the context of the present invention. When the device is worn on the limb P1 is already applied to the limb as a result of the pressure necessary to apply so as to keep the device on the limb. When the device compresses the limb, a compression build up is created as seen in view of slope 137. The pressure peaks at P2 after T1 has passed indicating the maximum squeezing pressure on the limb of the user during the compression transition period 139 (T1 to T2). As noted above, the length of the compression period 139 can be predetermined by the user or the device or a result of a plan and can be changed. The pressure applied to the limb effectively reduces or stops the venous return flow such that a low pressure is created in the venous system proximal to the compression location. At the end of the compression period 143 (T2), a slow release of the compressing element begins in view of slope 135 effectively resuming the blood and lymph flow in the venous system by slowly releasing the low pressure created proximal to the compression location during period of time T2 to T3. To generate a suction effect in the venous return of the blood and/or lymph system a quick release of the compressing element must be performed. The release of the compressing element in view of slope 136 is abrupt and is achieved by the length of time pressure is equalized proximal to the compression location. Thus, when release period T2 to T3 is relatively long, release period T5 to T6 is relatively short. Blood and/or lymph fluids are effectively sucked by the lower pressure situated proximal to the compression location allowing the return of blood and/or lymph flow more effectively during an abrupt release as is depicted in view of slope 136 compared with the relatively slower release depicted in view of slope 135. Thus, according to the preferred embodiment of the present invention P2 indicates the pressure on limb at the time the air cell is fully inflated. The transition time from the compressed state to the relaxed state according to the slow release mechanism is the difference between T2 and T3 and according to the fast release mechanism is the difference between T5 and T6. The fast release of the pressure and the short transition time from compressed state to the relaxed state provide the suction effect. Similarly, to the characteristic short transition time between compressed state to relaxed state presented in FIG. 6C fast relaxed to compressed state may be reached according to the device disclosed within the present invention. One skilled in the art will appreciate that the times shown, as well as the pressure applied in connection with FIG. 6C and the operation of the embodiments of the present invention can be varied to achieve the superior properties and enhanced features of the embodiments of the present invention. the FIGS. 7A, 7B, 7C present part of a mechanism that provides fast transition from compressed state to relaxation state through the use of a rotating cam and a piston for inflating or deflating the fluid cell. FIG. 7A shows a perspective view of the mechanism for inflating or deflating the fluid cell. FIG. 7B is a sectional view of the passing through the lines shown in view of side view of FIG. 7C. Mechanism 160 can replace vacuum chamber 120 as depicted in view of FIGS. 6A, 6B or the other embodiments above. Alternatively, mechanism 160 can be added to the inflating/deflating mechanism depicted in view of FIGS. 3A, 3B above. Mechanism 160 activates piston 180 mounted on a compressible spring 182. Spring 182 and piston 180 are positioned within chamber 170. Chamber 170 is connected with pipeline 172 to inflatable fluid cell 162. Edge 178 of rod 184 of piston 180 is positioned outside of chamber 170. Bearing 174 is pivotally connected to edge 178.

Cam 168 turns with pivot 166 pivotally connected to motor 164, said motor delivering rotational energy to said pivot 166. Cam 168 compresses piston 180 by compressing bearing 174. By compressing piston 180 fluid enters fluid cell 162 thus inflating the cell and compressing the limb of the user. An abrupt motion of piston 180 is reached when pivotally turned cam 168 reaches cusp 186. When the piston 180 reaches cusp 186, spring 182 is released, rod 184 moves proximal to the cam 168. Thus, the immediate relaxation of spring 182 causes the fluid inside fluid cell 162 to exit said fluid cell, either to the atmosphere or to a specially designated reservoir (not shown). The continued rotation of cam 168 enables a continuous cycle of inflating and deflating of fluid cell to provide compression forces to the limb and quick release of said compression forces to obtain a suction effect. Thus, mechanism 160 provides a fast transition from the compressed state to a relaxation state. One skilled in the art can appreciate that the suction effect is determined by the size of the cam used, the sealing ability of chamber 170, the size of piston 180, the size of chamber 170, the size of the designated reservoir as well as other parameters. Furthermore, one skilled in the art can appreciate that positioning pipe outlet 172 at the upper section of chamber 170 instead of its position shown in FIGS. 7A-7C allows the use of mechanism 160 for the fast transition from relaxation state to compressing state. Thus, the abrupt motion received from the interaction of cam 168 with piston 180 will convey fluid into fluid cell 162 generating an abrupt compression of the limb which can be instrumental in assisting the arterial flow of blood in the arterial system.

Figure 8:
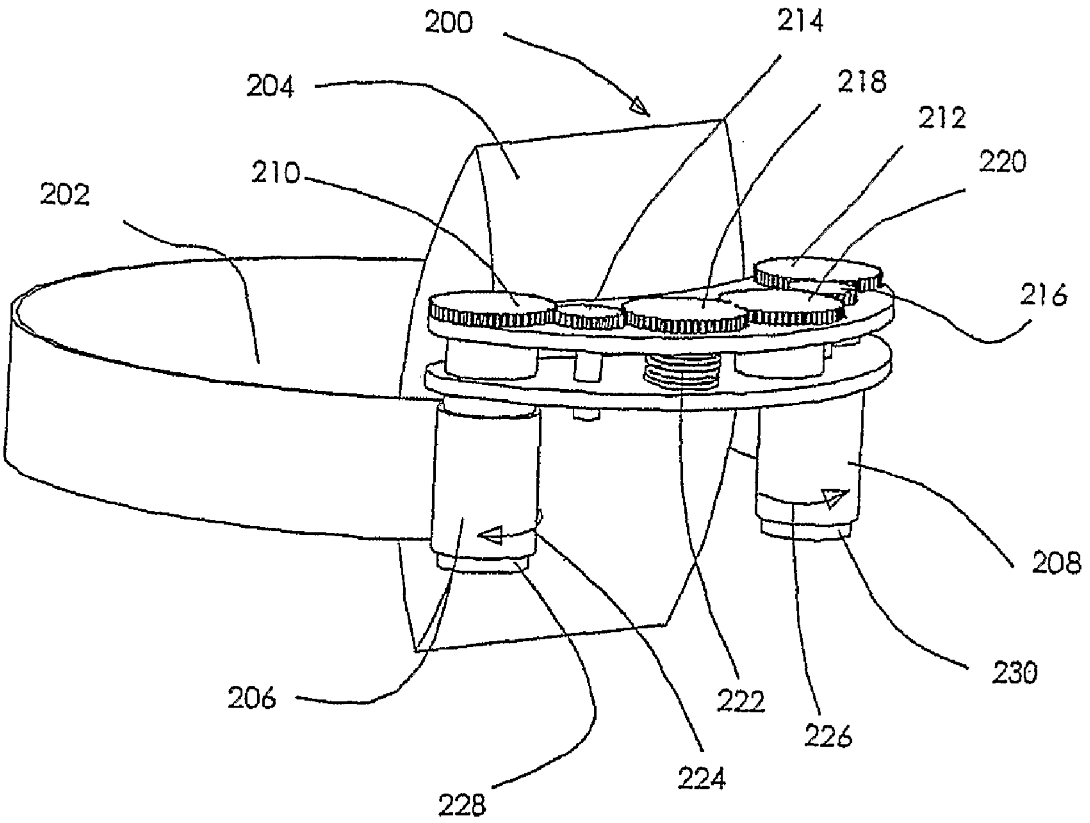
FIG. 8 is a fast release mechanism in accordance to one preferred embodiment of the present invention.

FIG. 8 shows another embodiment of the present invention for a fast release of compression on the limb, by showing a mechanism 200 for the fast release of strap 202. Mechanism 200 according to the present invention can be added to any of the above mentioned embodiments either associated with the inflating/deflating mechanism or separately, or alternatively, replace vacuum chamber 120 of FIG. 6B or mechanism 160 of FIGS. 7A, 7B. Mechanism 200 can be positioned in a separated housing or without housing as well. Mechanism 200 provides a fast release of straps during the transition from compressed state to relaxation state. Edges 206, 208 of strap 202 are rolled around roller pivots 228, 230, respectively. The rolling motivation of edges 206, 208 is reached by spring 222. Spring 222 can be charged by a small battery driven motor (not shown) applying rotational force to charge said spring. Spring 222 motivated turning of cogwheel 218 that in turn causes the turning of cogwheels 220, 216, 212 that turn pivot 230 in the direction of arrow 226. Similarly, the turning of cogwheel 218 causes the opposite direction turning, as indicated in arrow 224, of cogwheels 214, 210. Throughout the inflation of fluid cell 204 during the compressing mode strap 202 is stretched subject to the change of the perimeter caused by the inflating of fluid cell 204. Cogwheel 220 is provided with a clutch (not shown). Clutch of cogwheel is able to prevent the turning of cogwheel 220 opposite to the direction of arrow 226. The clutch can be mechanical or electronically controlled by a CPU that controls the operation of the entire inflation/deflation mechanism. Alternatively, the controller of the said clutch can be independent and be connected to a pressure gauge or a pressure sensor (not shown). According to the present embodiment spring 222 provides a force substantially weaker than the force applied to strap 202 as result of inflating air cell 204. Accordingly, releasing the clutch will provide an abrupt motion of release of straps around limb as presented in FIG. 2 above. One skilled in the art can appreciate that many variations of the suggested mechanism for fast release of strap can be suggested. Some of said embodiments can be fast release mechanism using a motor for releasing straps as well as many other embodiments.

Figure 9A:
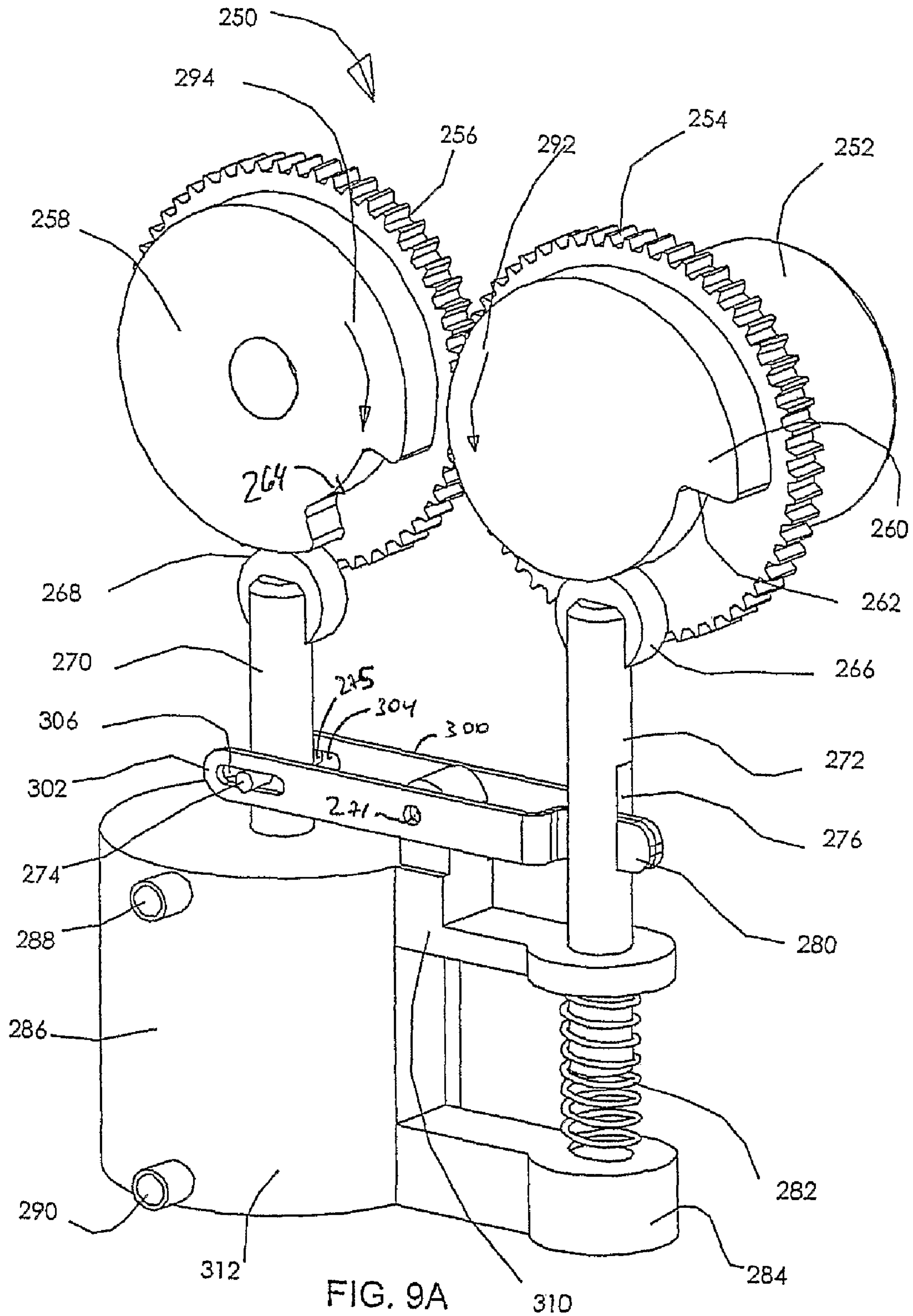

FIGS. 9A, 9B, 9C, 9D, 9E shows perspective views and a sectional view of a further embodiment for a mechanism for inflation/deflation of fluid cell through the use of an inflating/deflating chamber and cams moving in opposite directions one of said cams is of uneven shape and a cusp for providing fast transition between compressed state and relaxation state and vice versa. Mechanism 250 presented can be optionally positioned within a housing and be connected to an inflatable fluid or cell (not shown) positioned on a limb as shown and depicted in view of the Figs. above. Referring to FIG. 9A showing mechanism 250, cogwheels 254, 256 are mounted with cams 260, 258, respectively. Cogwheel 254 is pivotally connected to motor 252. Arrows 292, 294 indicate the turning directions of cams 260, 258, respectively. Motor 252 or any other driving mechanism drive cogwheel 254 and cam 260 in the direction of arrow 292. Since cogwheels 254 and 256 are connected, cogwheel 256 and cam 258 move in the opposite direction of arrow 292 and in the direction of arrow 294. Cam 260 comprises cusp 262 that allows abrupt movement of rod 272 as depicted below. Cam 258 is provided with depression 264. Depression 264 comprises two cusps that aid determining the movement of rod 270 and as a result the movement of piston 296 shown in FIG. 9B. Cams 258, 260 compress bearings 268, 266, respectively. Bearings 268, 266 are pivotally connected to the edge of rods 270, 272, respectively. Bearings 268, 266 are pivotally connected to the edge of rods 270, 272, respectively, thus allowing the movement of cams 260, 258 while in contact with bearings 268, 266 irrespective of the vertical direction of either one of rods 270, 272. Rods 270, 272 are connected one to the other via a forked shape connecting member 308 having a central pivot 271 enabling the vertical movement of rod 270 based on the vertical movement of rod 272 as is described below. Connecting member 308 is comprised from parallel tines 302, 304. Tines 302, 304 commence from a projecting end 280 of connecting member 308. Connecting member 308 is connected with a pivot (not shown) within bulge 278 to body element 310. Tines 300, 302 comprise openings 304, 306. Tines 300, 302 are positioned on two sides of rod 270. Rod 270 comprises projecting pins 274, 275 that are positioned within openings 306, 304, respectively. Openings 306, 304 provide movement within of pins 274, 275 resulting from movement of rod 270 along the vertical and horizontal planes as tines 300, 302 move through the movement of rod 272. Projecting end 280 is positioned within opening 276 within rod 272. Opening 276 provides movement of rod 272 and projecting end 280 in relation to each other, the size of opening 276 therefore also enables the length of movement of rod 270 through the movement of tines 300, 302. Rod 272 end is connected to spring 282 that is fixed to base 284. Spring 282 provides rod 272 a required flexibility preposition against the force applied by cam 260. Rod 270 is connected to piston 296 within chamber 286 as can be viewed in sectional view of FIG. 9B. Piston 296 compresses spring 298 within chamber 286. The force applied on spring 298 results from the movement of cam 258 and tines 300, 302. Chamber 286 is a sealed chamber such as depicted in view of FIGS. 6A, 7A above. Rapid movement of piston 296 provides rapid transition from compressed state to relaxation state and vice versa depending on the movement of rods 270, 272 which is restricted by depression 264 alignment vis-à-vis bearing 268 and cusp 262 alignment vis-à-vis bearing 266. Thus, rapid movement of piston 296 towards the bottom base of chamber 286 will convey fluid rapidly through fluid outlet 290. Similarly, a rapid movement of piston 296 towards the upper part of chamber 286 will result in the suction of fluid through fluid inlet 288. According to one preferred embodiment inlet 288 and outlet 290 are connected to an inflatable fluid cell (such as an air cell) as depicted in view of the above mentioned mechanisms. Thus, inlet 288 and outlet 290 can be connected to valves connected to controllers with CPU that controls the rate of the intermittently inflation and deflation of the cell (not shown) according to the present invention.

Figure 9B:
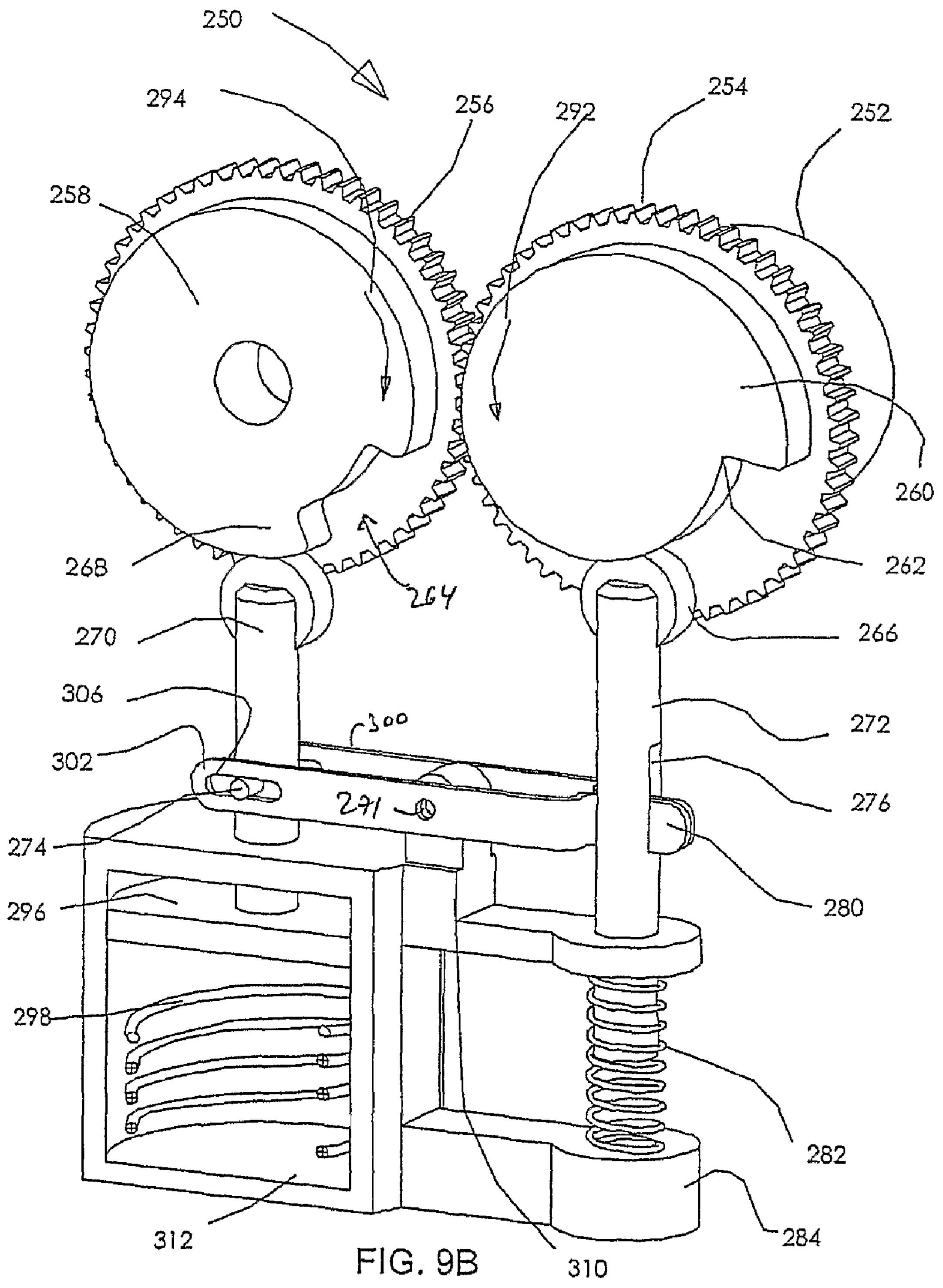
Figure 9C:
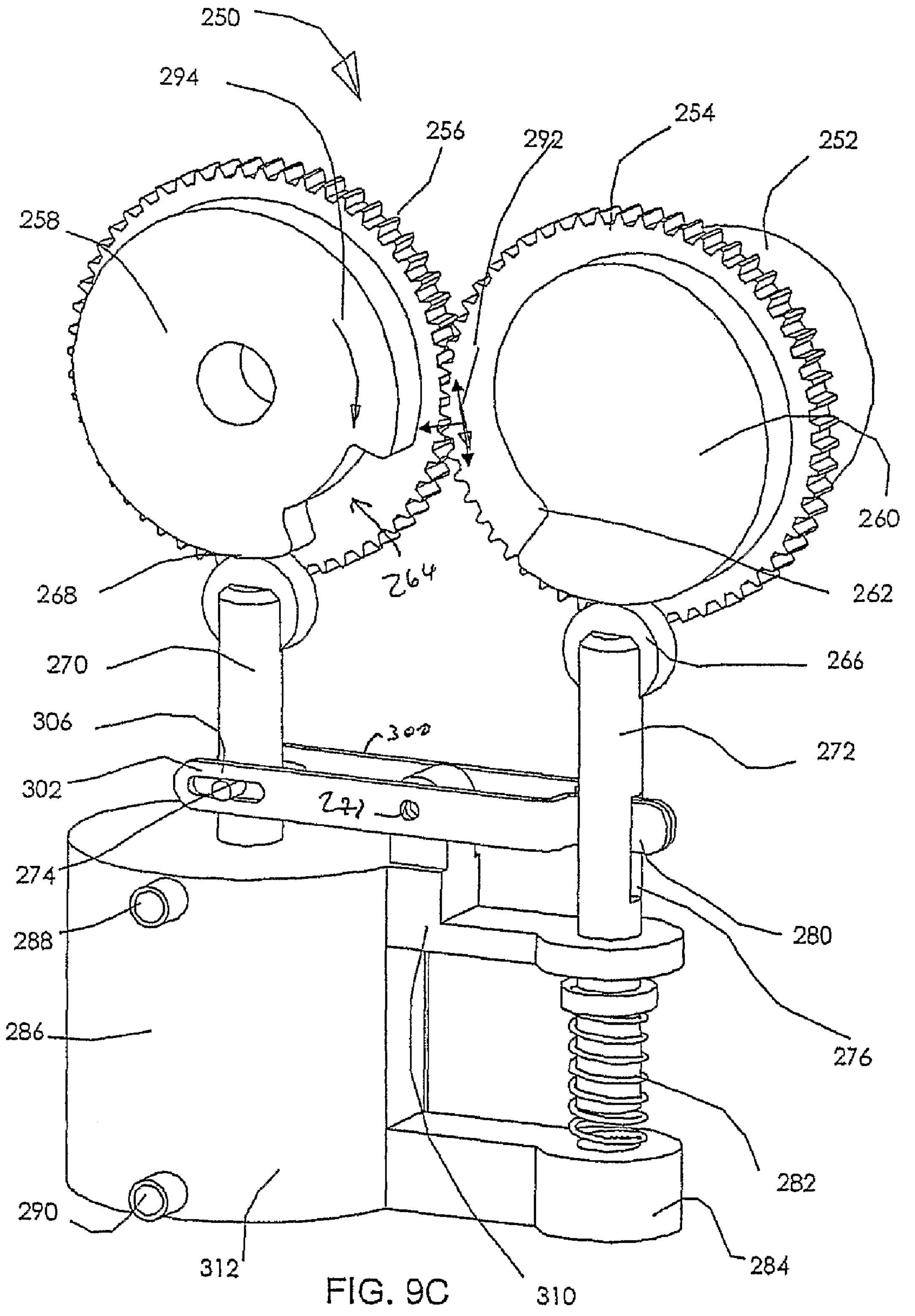
Figure 9D:
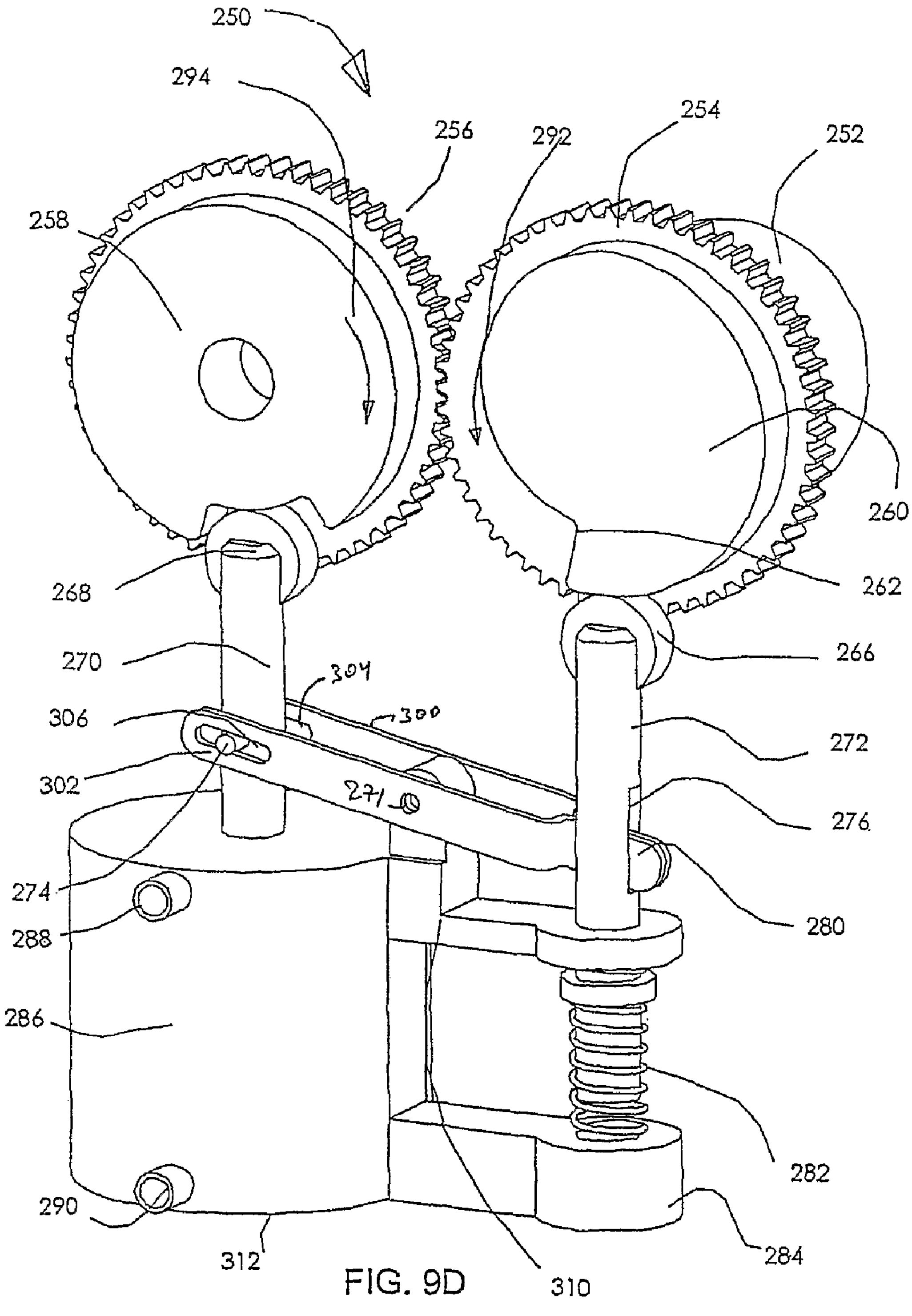

Mechanism 250 operating inflation and deflation of fluid cell (such as air cell) uses the mechanical movement of cams 260, 258 and the force applied to and from springs 282, 298, respectively to move times 300, 302 and piston 296 thus inflating or deflating the fluid cell. The operation of mechanism 250 is presented in FIGS. 9A-9E as follows: In FIGS. 9A, 9B show a perspective and sectional view of mechanism 250 a static state were neither of cams 258, 260 reached the position that provides abrupt movement is shown. Motor 252 or any other driving mechanism generates circular movement through a pivot (not shown) transferring rotational energy to cogwheel 254 and cam 260 which is associated there with. The rotational movement energy is in the direction of arrow 292. Since cogwheels 254 and 256 are in contact cogwheel 256 and cam 258 move in the opposite direction of arrow 292 and in the direction of arrow 294. The cams 258, 260 are aligned such that the alignment of depression 264 and bearing 268 will allow rod 270 to move laterally into depression 264 and thus move piston 296 in a lateral direction and fluid to enter the chamber 312. The movement of rod 280 is caused by the constant pressure on piston 296 generated by charged spring 298 in the vertical direction towards the cam 258. As shown in view of FIG. 9A the projecting end 280 of tines 300, 302 is in the lower position in opening 276 as rod 272 is constantly being vertically pushed by spring 282 towards cam 260. FIG. 9C shows a perspective view of mechanism 250 where the position of cams 258, 260 are at a position prior to bearing 268 entering depression 264. Cam 260 has completed about three quarters of a turn as compared to FIGS. 9A and 9B and as a result of the changing circumference of cam 260 the rod 272 is moved laterally in the direction of base 284 thus projecting end of tines 300, 302 is located at the upper end of opening 276 and the movement of rod 272 compresses and charges spring 282. Before cam 260 rotates such that it is aligned with bearing 266, cam 258 rotates such that depression 264 is aligned and is opposite to bearing 268 and as a result of the pressure applied by spring 298 piston 296 connected to rod 270 moves in the lateral direction moving bearing 268 into depression 264 driving tines 300, 302, in the up direction and projecting end 280 in the down direction. The movement of rod 270 in the up and vertical direction is abrupt and is determined by the shape of depression 2674 and the size of said depression. The rapid movement of piston 296 allows the suction of fluid from the fluid cell and enables the rapid release of the compression on the limb as is shown in view of the graph in FIG. 6C. Next, the cam 260 continues to rotate and the cusp 262 is aligned and is positioned directly opposite bearing 266 connected to rod 272 and spring 282 which is now charged. Spring 282 releases directional energy in the up direction causing rod 272 and bearing 266 to move in the up direction and into the cusp plain 262. As a result of the movement of rod 272 the projecting pin 280 is also pushed in the up direction and inversely moves tines 300, 302 in the down direction. Tines 300, 302 are connected via pins 274, 275 to rod 270 which in turn cause rod 272 to move in the down direction, bearing 268 to exist depression 264 and piston 296 to abruptly move in the down direction thus forcing the fluid in chamber 312 to exit via outlet 290 and inflate the fluid cell. While the figures discussed show both inlet 288 and outlet 290 it will be appreciated by those skilled in the art that a single inlet/outlet 290 can be used in a closed system to inflate or deflate a fluid cell or supply intermittent fluid pressure and suction to generate intermittent compression. If an inlet 288 and an outlet 290 are used, then in the embodiments shown when piston 296 is in the bottom position fluid has just exited chamber 312 and when piston 296 moves to the position closer to the upper part of chamber 312 then fluid may enter chamber 312 to be later pushed through outlet 290 effectively supplying continued fluid intermittent pumping. In such case piston 286 moves in the upper direction to a position superior to the position of inlet 288. In yet another alternative of the present invention using both an inlet 288 and an outlet 290 the mechanism 250 is used only for to evacuate the fluid in the fluid cell or to provide effectively intermittent suction of fluid. In such case when the piston 286 is moved in the up direction fluid is being sucked out of the fluid cell into chamber 312 via outlet 290. in such embodiment the outlet 288 is connected to another chamber (not shown) having a constant low pressure. Thus, when piston 296 is in the up position surpassing the position of outlet 288 the fluid existing the fluid cell and entering chamber 312 exists via inlet 288.

Mechanism 250 shown in the above Figs. uses a substantially reduced amount of energy for operating the air compression mechanism. A single battery operated motor or other cheap energy generating mechanisms including such mechanism having an energy storage there within can be used to drive the mechanism 250 for generating intermittent suction or pumping or a combination thereof. The use of less energy in operating mechanism 250 is possible due to the design of cam 260 having an energetic profile for charging spring 282 with kinetic energy. The circumference of cam 260 and the alignment of the cams respective to each other allow the use of the kinetic energy stored in both springs 298, 282 to effectively release the energy stored therein to move piston 296 in a vertical manner. The use of efficient energetic profiles enables the device to be small and efficient compared to presently available devices. As described in detail above, cam 260 revolves on its axis moving rod 272 in a downward movement so as to charge spring 282 with energy to be released and applied to the compression of fluid for the use with the mechanism 250. The use of specific profile for cam 260 allows an efficient charging of kinetic energy into spring 282 using a low power motor which can be operated by ordinary batteries or even other low power sources of energy such as solar cells and the like. Persons skilled in the art will appreciate that the form of cam 260 dictates the rate of charging of spring 282. In an alternative embodiment, cam 262 can have two charging cycles by having two cusps, such as cusp 262 and two or more depressions on cam 258 to allow the return of piston 296 to its initial position. In addition, the replacement of cam 260 with a cam having a mirror image energetic profile allows a slow release of piston 296 rather than the rapid compression. This and other like energetic profiles are seen in Israel Patent Application serial number 160185 filed on 2 Feb., 2004 titled "A PORTABLE DEVICE FOR THE ENHANCEMENT OF CIRCULATION OF BLOOD AND LYMPH FLOW IN A LIMB"; Israel Patent Application serial number 160214 filed on 4 Feb., 2004 titled "A PORTABLE DEVICE FOR THE ENHANCEMENT OF CIRCULATION OF BLOOD AND LYMPH FLOW IN A LIMB" which are incorporated herein by reference. The use of each energetic profile enables the device to operate efficiently while enabling slow and fast inflation and deflation of the air cell to allow intermittent compression of the limb.

In further embodiments of the present invention a device can comprise an actuating member such as any of the previously described above embodiments, and a power source that may be remotely positioned. Alternatively, other embodiments can comprise an actuating member as depicted above positioned adjacent to a limb, and a power source, and/or a controller, and/or a reservoir chamber that either can be positioned adjacent to said actuating member (e.g. an inflatable cell) or remotely positioned (e.g. on a hip or waist of user). Alternatively, each of the power source, controller, and reservoir can be positioned in a vicinity of user (e.g. on a stand or table). All mentioned embodiments can provide the abrupt transition from compressed state to relaxation state. Thus applying any of said devices on a limb provides that a suction effect will be achieved. The last embodiments and other features, aspects of the embodiments depicted hereinabove will become better understood with regard to the description of FIG. 10.

Figure 10:
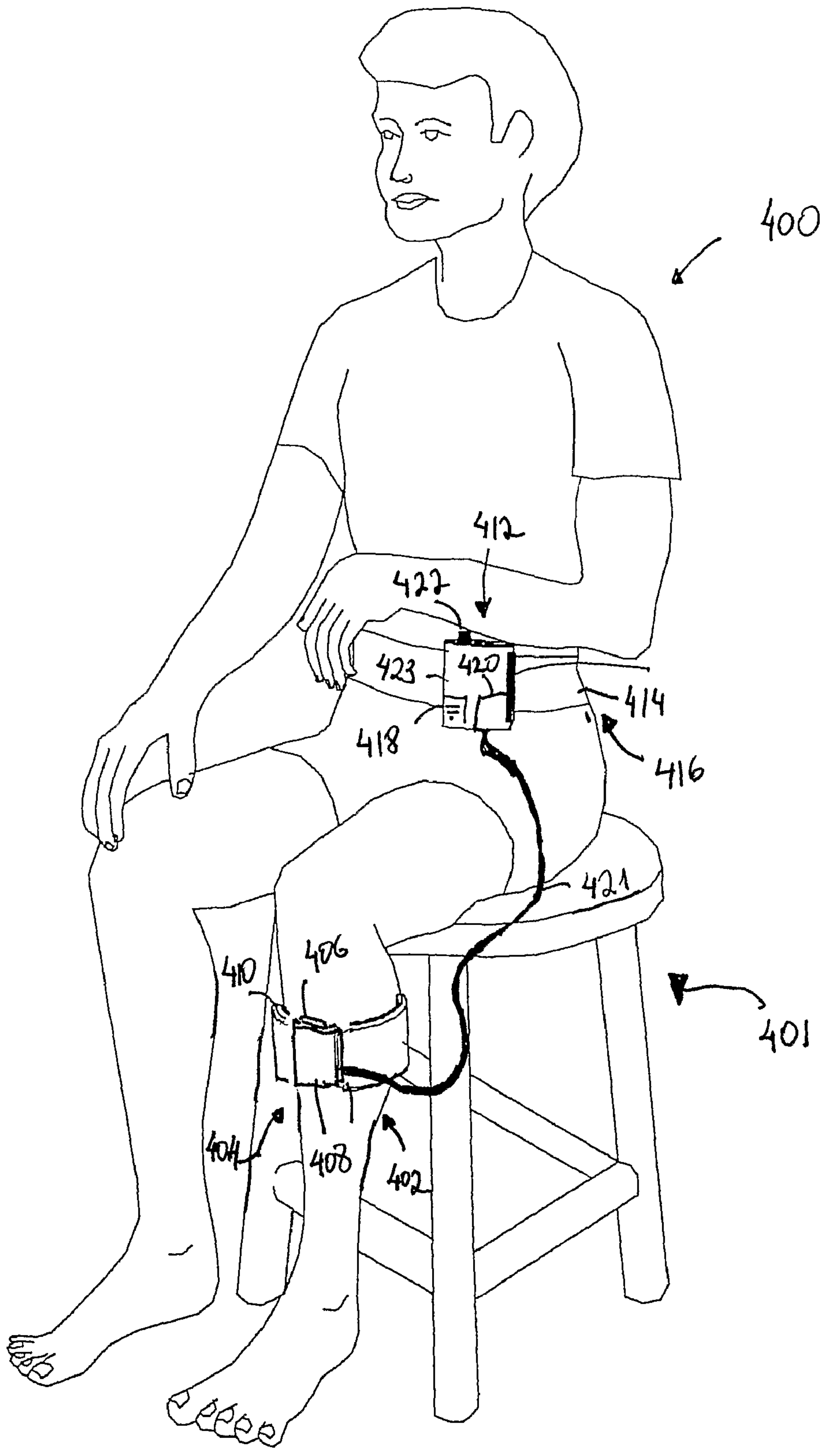
FIG. 10 is a pictorial illustration of a device in accordance with another preferred embodiment of the present invention.

FIG. 10 is a pictorial illustration of a device in accordance with another preferred embodiment of the present invention, wherein one or more of the components of a device 401 are remotely positioned from limb 402. User 400 is seated and has device 401 positioned adjacent to limb 402 and waist 416 of user. Device 401 comprises a first section 404, second section 412, and cord 421, wherein first section 404 is positioned adjacent to limb 402, second section 412 is attached to belt 414 adjacent to waist 416. Cord 421 connects sections 404, 412. Section 404 comprises strap 410, casing 408 and inflatable cell 406. Strap 410 can be a strap as described above in view of any of the above embodiments or as described in the applications incorporated to the present application. Strap 410 is connected to casing 408 and surrounds limb 402. Casing 408 comprises inflatable cell 406. Section 412 comprises a housing 423 with a pressure regulator 422 for regulating the pressure exerted on the limb during the compression phase. Housing 423 comprises a power source and the mechanism (not shown) for providing intermittent compression with abrupt transition between the squeezing and relaxing states as depicted in view of FIGS. 3A and 3B above. Alternatively, according to other embodiments housing 423 can comprise any of the mechanisms depicted above. Housing 423 comprises further an on/off switch 418 and outlet/inlet of fluid portion 420. Cord 421 may include one or more flexible fluid pipes (not shown) and one or more electric wires connecting said the mechanism within housing 423 with inflatable cell 406. Casing 408 can be fabricated from a rigid plastic material or any other material suitable for mounting inflatable cell 406 and strap 410 on limb 402.

Figure 11:
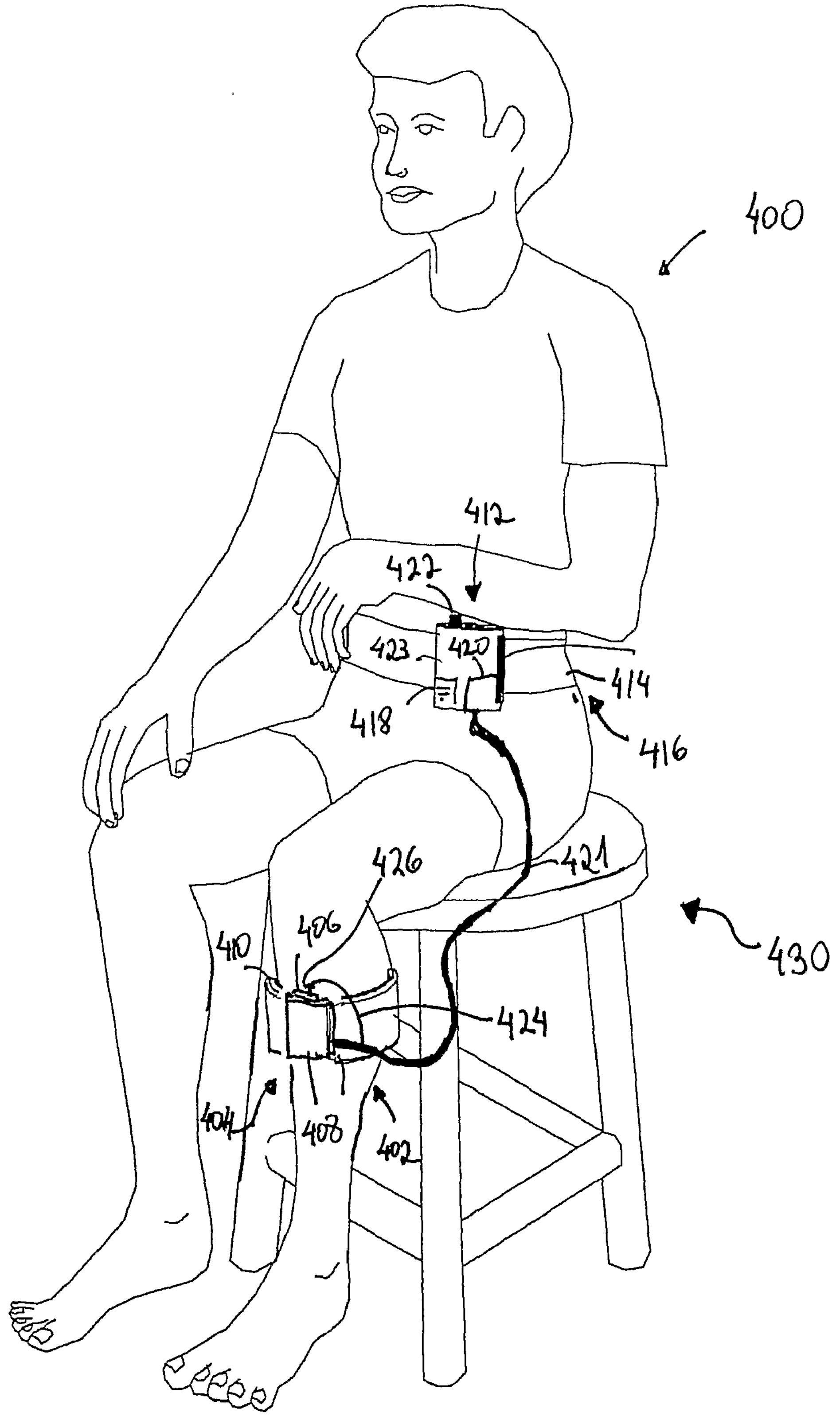
FIG. 11 is a pictorial illustration of a device in accordance with yet a further preferred embodiment of the present invention

FIG. 11 is a pictorial illustration of a device in accordance with another preferred embodiment of the present invention according to which a deflation valve 426, in communication with ambient atmosphere, is directly connected to cell 406. Valve 426 is controlled by unit 412 through wire 424. It will be realized that wire 424 is depicted separately for the sake of illustration only and that wire 424 may be completely inserted through cord 421. All other numerals in FIG. 11 indicate the same elements as in FIG. 10. In accordance with the embodiment of FIG. 11, deflation of cell 406 is performed by opening valve 426 to ambient atmosphere. The relatively small volume of cell 406 and the immediate opening of cell 406 to ambient atmosphere facilitates fast transition from high to low pressure.

One skilled in the art can appreciate that other embodiments can be demonstrating the present invention such as combination of the embodiments presented above. Furthermore, the embodiments provided are for demonstrating alone of the invention and are by no means limiting the scope of the present invention. Additionally, other embodiments using pneumatic, mechanical and a combination thereof can be implemented regarding to the invention It will be realized that the device of the present invention can be readily used for the enhancement of blood flow in many situations. Such include persons sitting or laying for long periods of time (for example, during long air flights or car travels or long hours working at the sitting position or immobilization at the hospital or rehabilitation center and the like.) It will be apparent that it may also be used for the enhancement of blood and lymph flow of a patient with diseases such as Diabetes Mellitus and Burger's disease. Also, for the enhancement of lymph flow in the hand of a patient post mastectomy and any other or like disease including all peripheral vascular disorders. Other uses not described here above will be apparent to the person skilled in the art. Providing said examples is made for the purpose of clarity and not limitation.

The reader's attention is directed to all documents and papers that are filed concurrently with the present specification and which are or will become open to public inspection with this specification, and the contents of such papers and documents are incorporated by reference herein. All the features disclosed in the specification, including the appending claims, abstract and drawings, may be replaced by alternative features serving the same equivalent or similar purpose, unless expressly stated otherwise. Although the present application has been described in considerable detail with reference to certain preferred embodiments, other embodiments and versions of those embodiments are possible and will not depart from the spirit or scope of the present invention. The same spirit and scope of the appended claims should not be limited to the description of the preferred embodiments contained herein.

I claim:

1. A portable device for modulating blood or lymph fluids or enhancing circulation in a body by generating intermittent squeezing forces on a limb, the device comprising:

a first actuating member having a proximal face and a distal face; said first actuating member provides controlled periodical change in volume of said actuating member such that the distal face of the actuating member moves relative to the limb; and a second actuating member having a rolling motivation connected to at least one adjustable strap or flap connectable to lateral ends of a rigid member for encircling the limb and for providing periodical movement such that the strap or flap is intermittently pulled in and out of said second actuating member;

thereby applying intermittent squeezing forces on the limb and modulating blood or lymph flow within said limb.

2. The device of claim 1 further comprising a clutch for preventing said second actuating member from releasing the at least one strap or flap.

3. The device of claim 2 wherein releasing the clutch provides an abrupt motion of release of said at least one strap or flap around limb, thereby creating a suction effect in the limb.

4. The device of claim 1 wherein the first actuating member is an at least one inflatable cell.

5. The device of claim 4 wherein the at least one inflatable cell can receive fluid.

6. The device of claim 4 wherein inflating and deflating the at least one inflatable cell provides cyclic transitions between a low-pressure relaxation phase and a high-pressure compression phase or high-pressure compression phase and a low-pressure relaxation phase.

7. The device of claim 5 wherein deflation of the at least one inflatable cell generates a suction effect assisting in blood or lymph flow within the body.

8. The device of claim 5 wherein inflation of the at least one inflatable cell generates pressure on the limb assisting in blood or lymph flow within the body.

9. The device of claim 5 wherein deflating of said at least one inflatable cell is performed abruptly.

10. The device of claim 4 wherein the rigid member is juxtaposed with the distal face of the at least one inflatable cell.

11. The device of claim 10 wherein the rigid member is applied to the limb.

12. The device of claim 10 wherein the rigid member is a housing.

13. The device of claim 1 further comprising a power source for supplying energy to said device.

14. The device of claim 13 wherein the power source is an at least one fluid compressor or a fluid pump.

15. The device of claim 13 wherein the power source is an at least one motor for providing energy to an at least one fluid compressor.

16. The device of claim 1 further comprising a controller for controlling operation of said first and second actuating members.

17. The device of claim 16 wherein the controller is a frequency regulator for controlling a frequency of an inflation deflation cycle.

18. The device of claim 16 wherein the controller is a central processing unit attached to a frequency regulator for controlling a frequency of an inflation deflation cycle.

19. The device of claim 16 wherein the controller is a mechanical controller.

20. The device of claim 1 wherein the first actuating member comprises an at least one chamber.

21. The device of claim 20 wherein the at least one chamber is rigid, or semi-rigid or flexible.

22. The device of claim 20 wherein the at least one chamber comprises a piston.

23. The device of claim 20 wherein the at least one chamber is elastic.

24. The device of claim 14 further comprising at least one valve for controlling fluid flow.

25. The device of claim 1 further comprising at least one valve for controlling fluid flow.

26. The device of claim 1 further comprising at least one motor, at least one chamber and at least one cam.

27. The device of claim 26 wherein at least one of the at least one chamber is rigid.

28. The device of claim 27 wherein the at least one of the at least one chamber further comprises a piston.

29. The device of claim 4 wherein the at least one adjustable strap or flap comprises the at least one inflatable cell.

30. The device of claim 1 further comprising a digital user interface.

31. The device of claim 30 wherein the digital user interface is positioned juxtaposed to the device.

32. The device of claim 30 wherein the digital user interface is positioned remotely from the device.

33. The device of claim 1 further comprising at least one pivot, at least two cogwheels and at least one spring.

34. The device of claim 1 wherein the at least one strap or flap are of varying width comprising one or more strips.

35. The device of claim 1 wherein the at least one strap or flap has at least one end thereof free to move around a corresponding connector such that the strap can be pulled by said end for tightening the strap around said limb.

36. The device of claim 35 wherein said at least one end can be anchored by fastening means.

37. The device of claim 4 wherein the at least one inflatable cell is disposable or replaceable.

38. The device of claim 1 further comprising a reservoir chamber for holding fluid to be provided to the first actuating member.

39. The device of claim 38 wherein the reservoir chamber comprises a piston.

40. The device of claim 38 wherein the reservoir chamber comprises one or more chambers.

41. The device of claim 38 wherein the reservoir chamber comprises an energy charged element.

42. The device of claim 38 wherein the reservoir chamber is a tank of constant volume.

43. The device of claim 1 further comprising a pressure gauge.

44. The device of claim 1 further comprising a pressure sensor.

45. The device of claim 1 further comprising a vacuum chamber for providing fast transition between inflated and deflated states of said first actuating member.

46. A portable device for modulating blood or lymph fluids or enhancing circulation in a body by generating intermittent squeezing forces on a limb, the device comprising:

at least one adjustable strap or flap for encircling the limb;

an actuating member having a proximal face and a distal face; said actuating member provides controlled periodical change in volume of said actuating member such that the distal face of the actuating member moves relative to the limb;

a vacuum chamber for providing fast transition between inflated and deflated states of said actuating member; and a vacuum pump to evacuate fluid from said vacuum chamber thus creating substantially a vacuum in said chamber;

thereby applying intermittent squeezing forces on the limb and modulating blood or lymph flow within said limb.

47. The device of claim 46 further comprising at least one valve for opening a conduit between said actuating member and said vacuum chamber, wherein fluid within said actuating member abruptly exists said actuating member and enters the vacuum chamber, whereby actuating member is deflated abruptly.

48. The device of claim 47 further comprising a controller for controlling said at least one valve.

49. A method for modulating blood or lymph fluids or enhancing circulation in a body by generating intermittent squeezing forces on a limb, the method comprising the steps of:

actuating an actuating member having a proximal face and a distal face;

encircling a limb with at least one adjustable strap or flap;

providing controlled periodical change in volume of said actuating member such that the distal face of the actuating member moves relative to the limb; and evacuating fluid from a vacuum chamber using a vacuum pump for creating substantially a vacuum in said vacuum chamber;

thereby applying intermittent squeezing forces on the limb and modulating blood or lymph flow within said limb.

50. The method of claim 49 wherein the actuating member is an at least one inflatable cell.

51. The method of claim 50 wherein the at least one inflatable cell can receive fluid.

52. The method of claim 49 further comprising the step of generating a suction effect assisting in blood or lymph flow within the body.

53. The method of claim 50 wherein deflating of said at least one inflatable cell is performed abruptly.

54. The method of claim 52 wherein the step of generating a suction effect comprises the steps of generating compression on the limb and abruptly releasing said compression by releasing the at least one strap or flap or by abruptly deflating the inflatable cell.

55. The method of claim 49 further comprising the step of controlling operation of the actuating member.

56. The method of claim 55 wherein the step of controlling comprises the step of regulating a frequency of an inflation deflation cycle of the actuating member.

57. The method of claim 49 further comprising the step of opening or closing at least one valve for controlling fluid flow.

58. The method of claim 49 further comprising the step of controlling the fluid flow through an at least one valve.

59. The method of claim 49 further comprising the step of actuating the at least one strap or flap.

60. The method of claim 59 wherein the step of actuating the at least one strap or flap comprises the step of pulling and releasing said at least one strap or flap.

61. The method of claim 50 further comprising the step of holding fluid to be provided to the at least one inflatable cell within a reservoir chamber.

62. The method of claim 61 further comprising the step of driving a piston within said reservoir chamber to inflate or deflate the at least one inflatable cell.

63. The method of claim 61 further comprising the step of charging an energy element within said reservoir chamber.

64. The method of claim 63 wherein the energy element is a spring.

65. The method of claim 49 further comprising the step of opening a conduit between said actuating member and said vacuum chamber, wherein fluid within said actuating member abruptly exists said actuating member and enters the vacuum chamber, whereby the actuating member is deflated abruptly.

* * * * *